US008278035B2

(12) United States Patent
Dawson et al.

(10) Patent No.: US 8,278,035 B2
(45) Date of Patent: Oct. 2, 2012

(54) METHOD AND SUBSTANCES FOR ISOLATING MIRNAS

(75) Inventors: Elliott P. Dawson, Murfreesboro, TN (US); Kristie E. Womble, Franklin, TN (US)

(73) Assignee: Bioventures, Inc., Murfreesboro, TN (US)

( * ) Notice: Subject to any disclaimer, the term of this patent is extended or adjusted under 35 U.S.C. 154(b) by 230 days.

(21) Appl. No.: 10/593,383

(22) PCT Filed: Aug. 18, 2006

(86) PCT No.: PCT/US2006/032264
§ 371 (c)(1),
(2), (4) Date: Sep. 19, 2006

(87) PCT Pub. No.: WO2007/024653
PCT Pub. Date: Mar. 1, 2007

(65) Prior Publication Data
US 2008/0160511 A1 Jul. 3, 2008

Related U.S. Application Data

(60) Provisional application No. 60/709,861, filed on Aug. 19, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6; 435/91.1; 435/91.31; 536/23.1; 536/24.3; 536/25.3; 935/78

(58) Field of Classification Search ............. 435/6, 91.1, 435/91.31; 536/23.1, 24.5, 25.4, 24.3, 25.3; 935/78
See application file for complete search history.

(56) References Cited

U.S. PATENT DOCUMENTS

| | | | | |
|---|---|---|---|---|
| 5,801,154 | A | * | 9/1998 | Baracchini et al. ......... 514/44 A |
| 2004/0175732 | A1 | | 9/2004 | Rana |
| 2005/0153347 | A1 | * | 7/2005 | Shapero et al. .............. 435/6 |
| 2005/0272075 | A1 | * | 12/2005 | Jacobsen et al. ............. 435/6 |

FOREIGN PATENT DOCUMENTS

| | | | |
|---|---|---|---|
| WO | 2005/003318 | A | 1/2005 |
| WO | 2006/014625 | A | 2/2006 |
| WO | 2006/033020 | A | 3/2006 |

OTHER PUBLICATIONS

Barken et al., "Effect of unlabeled helper probes on detection of an RNA target by bead-based sandwich hybridization," BioTechniques, 2004 vol. 36, pp. 142-132.
Tsai et al., "Nucleic acid capture assay, a new method for direct quantitation of nucleic acids," Nucleic Acids Research, 2003 vol. 31, No. 6, pp. 1-7.
Radovich et al., "Time-resolved fluorometric hybridization assays with RNA probes synthesized from polymerase chain reaction-generated DNA templates," Analytical Chemistry, 1995 vol. 67, No. 15, pp. 2644-2649.
International Search Report and Written Opinion dated Sep. 13, 2007, issued in parent International Patent Application No. PCT/US06/32264.
Barad Omer et al: "MicroRNA expression detected by oligonucleotide microarrays: system establishment and expression profiling in human tissues" Genome Research, Cold Spring Harbor Laboratory Press, Woodbury, NY, US, vol. 14, No. 12, Dec. 1, 2004, pp. 2486-2494, XP002420558 ISSN: 1088-9051.
Baskerville S. et al: "Microarray profiling of microRNAs reveals frequent coexpression with neighboring miRNAs and host genes," RNA, Cold Spring Harbor Laboratory Press, Woodbury, NY, US, Vool 11, No. 3, Mar. 1, 2005.
Grad Yonatan et al.: "Computational and experimental identification of *C. elegans* microRNAs" 20030501, vol. 11, No. 5, May 1, 2003, pp. 1253-1263, XP002284277.
Liang Ru-Qiang et al: "An oligonucleotide microarray for microRNA expression analysis based on labeling RNA with quantum dot and nanogold probe" Nucleic Acids Research, Oxford University Press, Surrey, GB, vol. 33, No. 2, Jan. 1, 2005, p. e17, XP002479454 ISSN: 0305-1048.
Liu Chang-Gong et al: "An oligonucleotide microchip for genome-wide microRNA profiling in human and mouse tissues" Proceedings of the National Academy of Sciences of USA, National Academy of Science, Washington, DC; US, vol. 101, No. 26, Jun. 29, 2004, pp. 9740-9744, XP002364908 ISSN: 0027-8424.
Sunkar Ralmanjulu et al: "Novel and stress-regulated microRNAs and other small RNAs from Arabidopsis" Plant Cell, American Society of Plant Physiologists, Rockville, MD, US, vol. 16, No. 8, Aug. 1, 2004, pp. 2001-2019, XP002450377 ISSN: 1040-4651.
Supplementary European Search Report and Search Opinion issued in related European Patent Application No. 06789847.8 on Oct. 24, 2008.
Corrected International Preliminary Report on Patentability (PCT/IPEA/409) issued by the PCT Authority in parent PCT Patent Application No. PCT/US06/32264 on May 13, 2009.

* cited by examiner

*Primary Examiner* — Jane Zara
(74) *Attorney, Agent, or Firm* — David A. Farah; Sheldon Mak & Anderson PC

(57) ABSTRACT

A capture probe suitable for use with a method for isolating miRNAs. A method for isolating an miRNA of interest from a sample comprising the miRNA of interest comprising providing the capture probe. A method for identifying an miRNA of interest.

53 Claims, 5 Drawing Sheets

SEQUENCE LISTING

<160> NUMBER OF SEQ ID NOS: 41

<210> SEQ ID NO 1
<211> LENGTH: 18
<212> TYPE: DNA
<213> ORGANISM: Artificial Sequence
<220> FEATURE:
<223> OTHER INFORMATION: synthetic adapter segment

<400> SEQUENCE: 1
atttaggtga cactatag                                             18

<210> SEQ ID NO 2
<211> LENGTH: 20
<212> TYPE: DNA
<213> ORGANISM: Artificial Sequence
<220> FEATURE:
<223> OTHER INFORMATION: synthetic adapter segment

<400> SEQUENCE: 2
ccctatagtg agtcgtatta                                           20

<210> SEQ ID NO 3
<211> LENGTH: 22
<212> TYPE: DNA
<213> ORGANISM: Artificial Sequence
<220> FEATURE:
<223> OTHER INFORMATION: synthetic miRNA binding segment

<400> SEQUENCE: 3
aactatacaa cctactacct ca                                        22

<210> SEQ ID NO 4
<211> LENGTH: 22

```
<212> TYPE: DNA
<213> ORGANISM: Artificial Sequence
<220> FEATURE:
<223> OTHER INFORMATION: synthetic miRNA binding segment

<400> SEQUENCE: 4
aaccacacaa cctactacct ca                                      22

<210> SEQ ID NO 5
<211> LENGTH: 22
<212> TYPE: DNA
<213> ORGANISM: Artificial Sequence
<220> FEATURE:
<223> OTHER INFORMATION: synthetic miRNA binding segment

<400> SEQUENCE: 5
aaccatacaa cctactacct ca                                      22

<210> SEQ ID NO 6
<211> LENGTH: 21
<212> TYPE: DNA
<213> ORGANISM: Artificial Sequence
<220> FEATURE:
<223> OTHER INFORMATION: synthetic miRNA binding segment

<400> SEQUENCE: 6
actatgcaac ctactacctc t                                       21

<210> SEQ ID NO 7
<211> LENGTH: 21
<212> TYPE: DNA
<213> ORGANISM: Artificial Sequence
<220> FEATURE:
<223> OTHER INFORMATION: synthetic miRNA binding segment

<400> SEQUENCE: 7
actatacaac ctcctacctc a                                       21

<210> SEQ ID NO 8
<211> LENGTH: 22
<212> TYPE: DNA
<213> ORGANISM: Artificial Sequence
<220> FEATURE:
<223> OTHER INFORMATION: synthetic miRNA binding segment

<400> SEQUENCE: 8
aactatacaa tctactacct ca                                      22

<210> SEQ ID NO 9
<211> LENGTH: 21
<212> TYPE: DNA
<213> ORGANISM: Artificial Sequence
<220> FEATURE:
<223> OTHER INFORMATION: synthetic miRNA binding segment

<400> SEQUENCE: 9
actgtacaaa ctactacctc a                                       21

<210> SEQ ID NO 10
<211> LENGTH: 21
<212> TYPE: DNA
<213> ORGANISM: Artificial Sequence
<220> FEATURE:
<223> OTHER INFORMATION: synthetic miRNA binding segment

<400> SEQUENCE: 10
acagcacaaa ctactacctc a                                       21
```

```
<210> SEQ ID NO 11
<211> LENGTH: 22
<212> TYPE: DNA
<213> ORGANISM: Artificial Sequence
<220> FEATURE:
<223> OTHER INFORMATION: synthetic miRNA binding segment

<400> SEQUENCE: 11
cacaagttcg gatctacggg tt                                              22

<210> SEQ ID NO 12
<211> LENGTH: 22
<212> TYPE: DNA
<213> ORGANISM: Artificial Sequence
<220> FEATURE:
<223> OTHER INFORMATION: synthetic miRNA binding segment

<400> SEQUENCE: 12
cttcagttat cacagtactg ta                                              22

<210> SEQ ID NO 13
<211> LENGTH: 61
<212> TYPE: DNA
<213> ORGANISM: Artificial Sequence
<220> FEATURE:
<223> OTHER INFORMATION: synthetic capture probe

<400> SEQUENCE: 13
atttaggtga cactatagaa actatacaac ctactacctc accctatagt gagtcgtatt     60
a                                                                     61

<210> SEQ ID NO 14
<211> LENGTH: 56
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
<222> LOCATION: (19)..(36)
<223> OTHER INFORMATION: n is a, c, g, or t

<400> SEQUENCE: 14
atttaggtga cactatagnn nnnnnnnnnn nnnnnnccct atagtgagtc gtatta         56

<210> SEQ ID NO 15
<211> LENGTH: 57
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
<222> LOCATION: (19)..(37)
<223> OTHER INFORMATION: n is a, c, g, or t

<400> SEQUENCE: 15
atttaggtga cactatagnn nnnnnnnnnn nnnnnnnccc tatagtgagt cgtatta        57

<210> SEQ ID NO 16
<211> LENGTH: 58
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
```

<222> LOCATION: (19)..(38)
<223> OTHER INFORMATION: n is a, c, g, or t

<400> SEQUENCE: 16
atttaggtga cactatagnn nnnnnnnnnn nnnnnnnncc ctatagtgag tcgtatta    58

<210> SEQ ID NO 17
<211> LENGTH: 59
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
<222> LOCATION: (19)..(39)
<223> OTHER INFORMATION: n is a, c, g, or t

<400> SEQUENCE: 17
atttaggtga cactatagnn nnnnnnnnnn nnnnnnnnnc cctatagtga gtcgtatta    59

<210> SEQ ID NO 18
<211> LENGTH: 60
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
<222> LOCATION: (19)..(40)
<223> OTHER INFORMATION: n is a, c, g, or t

<400> SEQUENCE: 18
atttaggtga cactatagnn nnnnnnnnnn nnnnnnnnnn ccctatagtg agtcgtatta    60

<210> SEQ ID NO 19
<211> LENGTH: 61
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
<222> LOCATION: (19)..(41)
<223> OTHER INFORMATION: n is a, c, g, or t

<400> SEQUENCE: 19
atttaggtga cactatagnn nnnnnnnnnn nnnnnnnnnn ncccta tagt gagtcgtatt    60 a    61

<210> SEQ ID NO 20
<211> LENGTH: 62
<212> TYPE: DNA
<213> ORGANISM: Artificial Sequence
<220> FEATURE:
<223> OTHER INFORMATION: synthetic capture probe
<220> FEATURE:
<221> NAME/KEY: misc_feature
<222> LOCATION: (19)..(42)
<223> OTHER INFORMATION: n is a, c, g, or t

<400> SEQUENCE: 20
atttaggtga cactatagnn nnnnnnnnnn nnnnnnnnnn nncccta tag tgagtcgtat    60 ta    62

<210> SEQ ID NO 21
<211> LENGTH: 60
<212> TYPE: DNA
<213> ORGANISM: Artificial Sequence

```
<220> FEATURE:
<223> OTHER INFORMATION: synthetic capture probe

<400> SEQUENCE: 21
atttaggtga cactatagaa ctatacaacc tcctacctca ccctatagtg agtcgtatta    60

<210> SEQ ID NO 22
<211> LENGTH: 63
<212> TYPE: DNA
<213> ORGANISM: Artificial Sequence
<220> FEATURE:
<223> OTHER INFORMATION: synthetic capture probe

<400> SEQUENCE: 22
atttaggtga cactatagag ctacctgcac tgtaagcact tttccctata gtgagtcgta    60
tta                                                                 63

<210> SEQ ID NO 23
<211> LENGTH: 60
<212> TYPE: DNA
<213> ORGANISM: Artificial Sequence
<220> FEATURE:
<223> OTHER INFORMATION: synthetic capture probe

<400> SEQUENCE: 23
atttaggtga cactatagac gcgtaccaaa agtaataatg ccctatagtg agtcgtatta    60

<210> SEQ ID NO 24
<211> LENGTH: 62
<212> TYPE: DNA
<213> ORGANISM: Artificial Sequence
<220> FEATURE:
<223> OTHER INFORMATION: synthetic capture probe

<400> SEQUENCE: 24
atttaggtga cactatagat cacataggaa taaaaagcca taccctatag tgagtcgtat    60
ta                                                                  62

<210> SEQ ID NO 25
<211> LENGTH: 56
<212> TYPE: DNA
<213> ORGANISM: Artificial Sequence
<220> FEATURE:
<223> OTHER INFORMATION: synthetic capture probe

<400> SEQUENCE: 25
atttaggtga cactatagag attcacaaca ccagctccct atagtgagtc gtatta        56

<210> SEQ ID NO 26
<211> LENGTH: 61
<212> TYPE: DNA
<213> ORGANISM: Artificial
<220> FEATURE:
<223> OTHER INFORMATION: synthetic capture probe

<400> SEQUENCE: 26
atttaggtga cactatagac gaaggcaaca cggataacct accctatagt gagtcgtatt    60
a                                                                   61

<210> SEQ ID NO 27
<211> LENGTH: 61
<212> TYPE: DNA
<213> ORGANISM: Artificial Sequence
<220> FEATURE:
<223> OTHER INFORMATION: synthetic capture probe
```

```
<400> SEQUENCE: 27
atttaggtga cactatagaa ataggtcaac cgtgtatgat tccctatagt gagtcgtatt    60
a                                                                    61

<210> SEQ ID NO 28
<211> LENGTH: 22
<212> TYPE: RNA
<213> ORGANISM: Homo sapiens

<400> SEQUENCE: 28
ugagguagua gguuguauag uu                                             22

<210> SEQ ID NO 29
<211> LENGTH: 21
<212> TYPE: RNA
<213> ORGANISM: Homo sapiens

<400> SEQUENCE: 29
ugagguagga gguuguauag u                                              21

<210> SEQ ID NO 30
<211> LENGTH: 24
<212> TYPE: RNA
<213> ORGANISM: Homo sapiens

<400> SEQUENCE: 30
aaaagugcuu acagugcagg uagc                                           24

<210> SEQ ID NO 31
<211> LENGTH: 21
<212> TYPE: RNA
<213> ORGANISM: Homo sapiens

<400> SEQUENCE: 31
cauuauuacu uuugguacgc g                                              21

<210> SEQ ID NO 32
<211> LENGTH: 23
<212> TYPE: RNA
<213> ORGANISM: Homo sapiens

<400> SEQUENCE: 32
uauggcuuuu uauuccuaug uga                                            23

<210> SEQ ID NO 33
<211> LENGTH: 22
<212> TYPE: RNA
<213> ORGANISM: Homo sapiens

<400> SEQUENCE: 33
uagguuaucc guguugccuu cg                                             22

<210> SEQ ID NO 34
<211> LENGTH: 22
<212> TYPE: RNA
<213> ORGANISM: Homo sapiens

<400> SEQUENCE: 34
uagguuaucc guguugccuu cg                                             22

<210> SEQ ID NO 35
<211> LENGTH: 22
```

```
<212> TYPE: RNA
<213> ORGANISM: Homo sapiens

<400> SEQUENCE: 35
aaucauacac gguugaccua uu                                              22

<210> SEQ ID NO 36
<211> LENGTH: 20
<212> TYPE: DNA
<213> ORGANISM: Artificial Sequence
<220> FEATURE:
<223> OTHER INFORMATION: synthetic linker segment

<400> SEQUENCE: 36
taatacgact cactataggg                                                 20

<210> SEQ ID NO 37
<211> LENGTH: 19
<212> TYPE: DNA
<213> ORGANISM: Artificial Sequence
<220> FEATURE:
<223> OTHER INFORMATION: synthetic linker segment

<400> SEQUENCE: 37
tctatagtgt cacctaaat                                                  19

<210> SEQ ID NO 38
<211> LENGTH: 20
<212> TYPE: DNA
<213> ORGANISM: Artificial Sequence
<220> FEATURE:
<223> OTHER INFORMATION: synthetic primer

<400> SEQUENCE: 38
cgatttaggt gacactatag                                                 20

<210> SEQ ID NO 39
<211> LENGTH: 20
<212> TYPE: DNA
<213> ORGANISM: Artificial Sequence
<220> FEATURE:
<223> OTHER INFORMATION: synthetic primer

<400> SEQUENCE: 39
taatacgact cactataggg                                                 20

<210> SEQ ID NO 40
<211> LENGTH: 18
<212> TYPE: DNA
<213> ORGANISM: Artificial Sequence
<220> FEATURE:
<223> OTHER INFORMATION: synthetic primer

<400> SEQUENCE: 40
gtaaaacgac ggccagtg                                                   18

<210> SEQ ID NO 41
<211> LENGTH: 20
<212> TYPE: DNA
<213> ORGANISM: Artificial Sequence
<220> FEATURE:
<223> OTHER INFORMATION: synthetic primer

<400> SEQUENCE: 41
ggaaacagct atgaccatga                                                 20
```

METHOD AND SUBSTANCES FOR ISOLATING MIRNAS

CROSS-REFERENCE TO RELATED APPLICATIONS

The present application is a 371 of International Patent Application No. PCT/US06/32264, titled "Method and Substances for Isolating miRNAs," filed Aug. 18, 2006, which claims the benefit of U.S. Provisional Patent Application 60/709,861, titled "Method and Substances for the Isolation, Amplification and Detection of miRNAs," filed Aug. 19, 2005, the contents of which are incorporated in this disclosure by reference in their entirety.

BACKGROUND

MicroRNAs (miRNAs) are small, generally between 18 and 24 residues, polyribonucleotides derived from longer hairpin noncoding transcripts in eukaryotes. miRNAs play a significant role in cellular developmental and differentiation pathways. Consequently, there have been considerable efforts made to understand and characterize the temporal, spatial and cellular expression levels and patterns of expression of miRNAs to ascertain their precise role in cellular development and differentiation in both normal and disease states.

miRNAs are currently studied by, first, obtaining the total RNA from a sample. Next, the total RNA is fractionated into subpopulations by gel electrophoresis or by chromatographic fractionation and size selective elution. Then, the appropriate section of the gel is cut, and the 18-24 RNAs are eluted from the gel, or the eluted fraction containing single stranded RNAs in the size range of 18-24 ribonucleotides is collected. Next, the RNAs are isolated by precipitation and the miRNAs are characterized.

Disadvantageously, however, these methods do not work well when the amount of sample is small, such as samples from tumor tissue or biopsy material. Further, characterization of the miRNAs isolated by present methods usually comprises a several step amplification procedure followed by detection, quantitation, cloning and sequencing. Because of the large number of steps in these processes and the notorious inefficiencies associated with the repeated purification, the isolation and identification of miRNAs using present methods is time consuming, relatively expensive, requires relatively large amounts of material and is not fully representative of the population of miRNAs expressed within a small sample, such as within a biopsy of a tumor. Additionally, the present methods are not specific to isolating and identifying an miRNA, and therefore, often isolate and identify siRNA, tRNA, 5S/5.8SrRNA and degraded RNA from additional cellular RNAs.

Therefore, there is the need for an improved method for isolation and identification of miRNAs that is not associated with these disadvantages.

SUMMARY

According to one embodiment of the present invention, there is provided a capture probe suitable for use with a method for isolating miRNAs. The capture probe comprises: a) a first adapter segment having a first adapter segment sequence, the first adapter segment comprising a 3' end and a 5' end; b) a second adapter segment having a second adapter segment sequence, the second adapter segment comprising a 3' end and a 5' end; and c) an miRNA binding segment having an miRNA binding segment sequence, where the miRNA binding segment is substantially complementary to, and capable of hybridizing to, one or more than one miRNA of interest by Watson-Crick base pairing, where the 5' end of the first adapter segment is connected to the 3' end of the miRNA binding segment, and where the 3' end of the second adapter segment is connected to the 5' end of the miRNA binding segment.

In one embodiment, the capture probe comprises a substance selected from the group consisting of one or more than one type of polynucleotide, one or more than one type of polynucleotide analog, and a combination of one or more than one type of polynucleotide and polynucleotide analog.

According to another embodiment of the present invention, there is provided a set of capture probes, where each of the capture probes of the set of capture probes is a capture probe according to the present invention, where each of the capture probes comprises identical first adapter segment sequences, where each of the capture probes of the set of capture probes comprises identical miRNA binding segment sequences, and where each of the capture probes of the set of capture probes comprises identical second adapter segment sequences.

According to another embodiment of the present invention, there is provided a set of capture probes, where each of the capture probes is a capture probe according to the present invention, and where the set comprises at least one capture probe comprising an miRNA binding segment that is substantially complementary to, and capable of hybridizing to, each miRNA from a single public database.

According to another embodiment of the present invention, there is provided a set of capture probes, where each of the capture probes is a capture probe according to the present invention, where the set comprises a first capture probe and a second capture probe, where the first capture probe and the second capture probe have identical first adapter segment sequences, where the first capture probe and the second capture probe have identical miRNA binding segment sequences, and where the first capture probe has a second adapter segment sequence that is different from the second adapter segment sequence of the second capture probe.

According to another embodiment of the present invention, there is provided a set of capture probes, where each of the capture probes is a capture probe according to the present invention, where the set comprises a first capture probe and a second capture probe, where the first capture probe and the second capture probe have identical first adapter segment sequences, where the first capture probe and the second capture probe have identical second adapter segment sequences, and where the first capture probe has an miRNA binding segment sequence that is different from the miRNA binding segment sequence of the second capture probe.

According to another embodiment of the present invention, there is provided a set of capture probes, where each of the capture probes is a capture probe according to the present invention, where the set comprises a first capture probe and a second capture probe, where the first capture probe and the second capture probe have identical miRNA binding segment sequences, where the first capture probe and the second capture probe have identical second adapter segment sequences, and where the first capture probe has a first adapter segment sequence that is different from the first adapter segment sequence of the second capture probe.

According to another embodiment of the present invention, there is provided a set of capture probes, where each of the capture probes is a capture probe according to the present invention, where the set comprises a first capture probe and a second capture probe, where the first capture probe and the second capture probe have identical first adapter segment sequences, where the first capture probe has an miRNA binding segment sequence that is different from the miRNA binding segment sequence of the second capture probe, and where the first capture probe has a second adapter segment sequence that is different from the second adapter segment sequence of the second capture probe.

According to another embodiment of the present invention, there is provided a set of capture probes, where each of the capture probes is a capture probe according to the present invention, where the set comprises a first capture probe and a second capture probe, where the first capture probe and the second capture probe have identical miRNA binding segment sequences, where the first capture probe has a first adapter segment sequence that is different from the first adapter segment sequence of the second capture probe, and where the first capture probe has a second adapter segment sequence that is different from the second adapter segment sequence of the second capture probe.

According to another embodiment of the present invention, there is provided a set of capture probes, where each of the capture probes is a capture probe according to the present invention, where the set comprises a first capture probe and a second capture probe, where the first capture probe and the second capture probe have identical second adapter segment sequences, where the first capture probe has a first adapter segment sequence that is different from the first adapter segment sequence of the second capture probe, and where the first capture probe has a miRNA binding segment sequence that is different from the miRNA binding segment sequence of the second capture probe.

According to another embodiment of the present invention, there is provided a set of capture probes, where each of the capture probes is a capture probe according to the present invention, where the set comprises a first capture probe and a second capture probe, where the first capture probe has a first adapter segment sequence that is different from the first adapter segment sequence of the second capture probe, where the first capture probe has an miRNA binding segment sequence that is different from the miRNA binding segment sequence of the second capture probe, and where the first capture probe has a second adapter segment sequence that is different from the second adapter segment sequence of the second capture probe.

According to another embodiment of the present invention, there is provided a capture probe according to the present invention, where the first adapter segment, or the second adapter segment, or both the first adapter segment and the second adapter segment are between 6 and 16 residues.

According to another embodiment of the present invention, there is provided a capture probe according to the present invention, where the first adapter segment, or the second adapter segment, or both the first adapter segment and the second adapter segment further comprise a sequence that is a polynucleotide synthesis promoter motif for a polynucleotide polymerase, or that is complementary to a polynucleotide synthesis promoter motif for a polynucleotide polymerase. In one embodiment, the polynucleotide synthesis promoter motif is a motif for a polynucleotide synthesis promoter selected from the group consisting of T7, SP6, a T3 DNA dependent RNA polymerase, a type 2 RNA polymerase of *E. coli* and single stranded DNA dependent N4 RNA polymerase.

According to another embodiment of the present invention, there is provided a capture probe according to the present invention, where the first adapter segment, or the second adapter segment, or both the first adapter segment and the second adapter segment further comprise a restriction site motif. In one embodiment, the restriction site motif is acted upon by a restriction enzyme selected from the group consisting of Not I, Xho I, Xma I and Nhe I.

According to another embodiment of the present invention, there is provided a capture probe according to the present invention, where the first adapter segment, or the second adapter segment, or both the first adapter segment and the second adapter segment further comprise a solid phase binding group to immobilize the capture probe to a solid phase. In one embodiment, the solid phase binding group is at or near the 3' end of the first adapter segment. In another embodiment, the solid phase binding group is at or near the 5' end of the second adapter segment. In another embodiment, the solid phase binding group immobilizes the capture probe to the solid phase covalently. In another embodiment, the solid phase binding group immobilizes the capture probe to the solid phase non-covalently. In another embodiment, the solid phase binding group comprises biotin or an analog of biotin.

According to another embodiment of the present invention, there is provided a capture probe according to the present invention, where the miRNA binding segment consists of 18 or 19 or 20 or 21 or 22 or 23 or 24 residues selected from the group consisting of DNA, RNA, chimeric DNA/RNA, DNA analogs and RNA analogs. In another embodiment, the miRNA of interest that the miRNA binding segment is substantially complementary to, and capable of hybridizing to, is selected from a public database. In another embodiment, the miRNA of interest is a eucaryotic miRNA. In another embodiment, the miRNA of interest is a primate miRNA. In another embodiment, the miRNA of interest is a human miRNA. In another embodiment, the miRNA binding segment is exactly the complement to the miRNA of interest in both length and sequence. In another embodiment, the miRNA binding segment is more than 90% complementary to a segment of the miRNA of interest of the same length as the miRNA of interest sequence. In another embodiment, the miRNA binding segment is more than 80% complementary to a segment of the miRNA of interest of the same length as the miRNA of interest sequence. In another embodiment, the first adapter segment has a first adapter segment sequence according to SEQ ID NO:1. In another embodiment, the second adapter segment has a second adapter segment sequence according to SEQ ID NO:2.

According to another embodiment of the present invention, there is provided a method for isolating an miRNA of interest from a sample comprising the miRNA of interest. The method comprises: a) providing a sample comprising the miRNA of interest; b) providing a capture probe according to the present invention; c) providing a first linker and a second linker; d) combining the sample, the capture probe, the first linker and the second linker; e) allowing the first linker to hybridize with the first adapter segment, the miRNA of interest to hybridize with the miRNA binding segment, and the second linker to hybridize with the second adapter segment; f) ligating the 3' end of the first linker that is hybridized to the first adapter segment to the 5' end of the miRNA of interest that is hybridized to the miRNA binding segment, and ligating the 3' end of the miRNA of interest that is hybridized to the miRNA binding segment to the 5' end of the second linker that is hybridized to the second adapter segment, thereby producing a complex defined as a strand of first linker, miRNA of interest and second linker that have been ligated together (ligated first linker-miRNA of interest-second linker) and that is hybridized to the capture probe; and g) dehybridizing the capture probe from the strand of the ligated first linker-miRNA of interest-second linker, where the miRNA of interest has an miRNA of interest sequence, and comprises a 3' end and a 5' end, where the miRNA of interest is substantially complementary to, and capable of hybridizing to, the miRNA binding segment of the capture probe by Watson-Crick base pairing, where the first linker has a first linker sequence, and comprises a 3' end and a 5' end, where the first linker is substantially complementary to, and capable of hybridizing to, the first adapter segment of the capture probe by Watson-Crick base pairing, where the second linker has a second linker sequence, and comprises a 3' end and a 5' end, and where the second linker is substantially complementary to, and capable of hybridizing to, the second adapter segment of the capture probe by Watson-Crick base pairing. In another embodiment, the sample further comprises one or more than one substance that is chemically related to the miRNA of interest selected from the group consisting of an RNA other than miRNA and a DNA. In another embodiment, the sample is from a eukaryote. In another embodiment, the sample is from a primate. In another embodiment, the sample is from a human. In another embodiment, the sample comprises a tissue or fluid selected from the group consisting of blood, brain, heart, intestine, liver, lung, pancreas, muscle, a leaf, a flower, a plant root and a plant stem. In another embodiment, the miRNA of interest consists of 18 or 19 or 20 or 21 or 22 or 23 or 24 RNA residues. In one embodiment, the miRNA of interest is listed in a public database. In another embodiment, the sample provided comprises a plurality of miRNAs of interest, and each of the plurality of miRNAs of interest have miRNA of interest sequences that are identical to one another. In another embodiment, the sample provided comprises a plurality of miRNAs of interest comprising a first miRNA of interest having a first miRNA of interest sequence, and a second miRNA of interest having a second miRNA of interest sequence, and where the first miRNA of interest sequence is different from the second miRNA of interest sequence. In another embodiment, the sample provided comprises a plurality of miRNAs of interest comprising a first miRNA of interest having a first miRNA of interest sequence, a second miRNA of interest having a second miRNA of interest sequence, and a third miRNA of interest having a third miRNA of interest sequence, where the first miRNA of interest sequence is different from the second miRNA of interest sequence, where the first miRNA of interest sequence is different from the third miRNA of interest sequence, and where second miRNA of interest sequence is different from the third miRNA of interest sequence. In another embodiment, the method further comprises isolating the total RNA from the sample after providing the sample.

In one embodiment, the capture probe provided is a set of capture probes, where each of the capture probes comprises identical first adapter segment sequences, where each of the capture probes of the set of capture probes comprises identical miRNA binding segment sequences, and where each of the capture probes of the set of capture probes comprises identical second adapter segment sequences. In another embodiment, the capture probe provided is a set of capture probes, where the set comprises at least one capture probe comprising an miRNA binding segment that is substantially complementary to, and capable of hybridizing to, each miRNA listed in a single public database. In another embodiment, the capture probe provided is a set of capture probes, where the set comprises a first capture probe and a second capture probe, where the first capture probe and the second capture probe have identical first adapter segment sequences, where the first capture probe and the second capture probe have identical miRNA binding segment sequences, and where the first capture probe has a second adapter segment sequence that is different from the second adapter segment sequence of the second capture probe. In another embodiment, the capture probe provided is a set of capture probes, where the set comprises a first capture probe and a second capture probe, where the first capture probe and the second capture probe have identical first adapter segment sequences, where the first capture probe and the second capture probe have identical second adapter segment sequences, and where the first capture probe has an miRNA binding segment sequence that is different from the miRNA binding segment sequence of the second capture probe. In another embodiment; the capture probe provided is a set of capture probes, where the set comprises a first capture probe and a second capture probe, where the first capture probe and the second capture probe have identical miRNA binding segment sequences, where the first capture probe and the second capture probe have identical second adapter segment sequences, and where the first capture probe has a first adapter segment sequence that is different from the first adapter segment sequence of the second capture probe. In another embodiment, the capture probe provided is a set of capture probes, where the set comprises a first capture probe and a second capture probe, where the first capture probe and the second capture probe have identical first adapter segment sequences, where the first capture probe has an miRNA binding segment sequence that is different from the miRNA binding segment sequence of the second capture probe, and where the first capture probe has a second adapter segment sequence that is different from the second adapter segment sequence of the second capture probe. In another embodiment, the capture probe provided is a set of capture probes, where the set comprises a first capture probe and a second capture probe, where the first capture probe and the second capture probe have identical miRNA binding segment sequences, where the first capture probe has a first adapter segment sequence that is different from the first adapter segment sequence of the second capture probe, and where the first capture probe has a second adapter segment sequence that is different from the second adapter segment sequence of the second capture probe. In another embodiment, the capture probe provided is a set of capture probes, where the set comprises a first capture probe and a second capture probe, where the first capture probe and the second capture probe have identical second adapter segment sequences, where the first capture probe has a first adapter segment sequence that is different from the first adapter segment sequence of the second capture probe, and where the first capture probe has an miRNA binding segment sequence that is different from the miRNA binding segment sequence of the second capture probe. In another embodiment, the capture probe provided is a set of capture probes, where the set comprises a first capture probe and a second capture probe, where the first capture probe has a first adapter segment sequence that is different from the first adapter segment sequence of the second capture probe, where the first capture probe has an miRNA binding segment sequence that is different from the miRNA binding segment sequence of the second capture probe, and where the first capture probe has an miRNA binding segment sequence that is different from the miRNA binding segment sequence of the second capture probe. In another embodiment, the capture probe provided is a set of capture probes, where the set comprises a first capture probe having a first capture probe sequence, a second capture probe having a second capture probe sequence, and a third capture probe having a third capture probe sequence, where the first capture probe sequence is different from the second capture probe sequence, where the first capture probe sequence is different from the third capture probe sequence, and where second capture probe sequence is different from the third capture probe sequence.

In one embodiment, the first linker segment and the second linker segment comprise a substance selected from the group consisting of one or more than one type of polynucleotide, one or more than one type of polynucleotide analog, and a combination of one or more than one type of polynucleotide and polynucleotide analog. In another embodiment, the first linker, or the second linker, or both the first linker and the second linker are resistant to nuclease degradation. In another embodiment, the first linker, or the second linker, or both the first linker and the second linker comprise nuclease resistant nucleotides. In another embodiment, the first linker, or the second linker, or both the first linker and the second linker comprise nucleotides with a phosphothioate backbone that render the first linker, or the second linker, or both the first linker and the second linker resistant to nuclease degradation. In another embodiment, the first linker, or the second linker, or both the first linker and the second linker comprise nuclease resistant nucleotides and comprise nucleotides with a phosphothioate backbone that render the first linker, or the second linker, or both the first linker and the second linker resistant to nuclease degradation. In another embodiment, the first linker and the second linker, each comprises between 6 and 50 residues. In another embodiment, the first linker comprises at least 10 residues, and at least 10 residues at the 3' end of the first linker are exactly the complement of the corresponding residues at or near the 5' end of the first adapter segment. In another embodiment, the second linker comprises at least 10 residues, and at least 10 residues at the 5' end of the second linker are exactly the complement of the corresponding residues at or near the 3' end of the second adapter segment. In another embodiment, the 5' end of the first linker, or the 3' end of the second linker, or both the 5' end of the first linker and the 3' end of the second linker comprise a label. In another embodiment, the 5' end of first linker comprises one or more than one residue that extends beyond the 3' end of the first adapter segment after the first linker hybridizes to the first adapter segment. In one embodiment, the one or more than one residue of the 5' end of first linker that extends beyond the 3' end of the first adapter segment functions as a primer binding site. In another embodiment, the 3' end of second linker comprises one or more than one residue that extends beyond the 5' end of the second adapter segment after the second linker hybridizes to the second adapter segment. In one embodiment, the one or more than one residue of the 3' end of second linker that extends beyond the 5' end of the second adapter segment functions as a primer binding site. In another embodiment, the sample, the capture probe, the first linker and the second linker are combined simultaneously.

In one embodiment, the method further comprises adding one or more than one RNAse inhibitor to the combination of the sample, the capture probe, the first linker and the second linker. In another embodiment, the first adapter segment comprises a solid phase binding group, or the second adapter segment comprises a solid phase binding group, or both the first adapter segment comprises a solid phase binding group and the second adapter segment comprises a solid phase binding group, and the method further comprises binding the capture probe to a solid phase before or after combining the sample, the capture probe, the first linker and the second linker. In another embodiment, the solid phase is a plurality of paramagnetic particles. In another embodiment, the capture probe is bound to a solid phase through the first adapter segment or through the second adapter segment or through both the first adapter segment and the second adapter segment, and the method further comprises purifying the capture probes with hybridized first linker, miRNA of interest and second linker—bound to the solid phase by removing non-hybridized first linkers, second linkers and any other substances that are not bound to the solid phase. In another embodiment, the solid phase is contained in a vessel comprising a surface and a cap, and purifying comprises applying a magnetic field to attract the solid phase to the surface of the vessel or the cap of the vessel. In another embodiment, the first linker hybridizes to the first adapter segment at a position where the last residue on the 3' end of the first linker hybridizes to a residue on the first adapter segment that is between 1 residue and 5 residues from the 3' end of the miRNA binding segment. In another embodiment, the first linker hybridizes to the first adapter segment at a position where the last residue on the 3' end of the first linker hybridizes to a residue on the first adapter segment that is immediately adjacent to the 3' end of the miRNA binding segment. In another embodiment, the second linker hybridizes to the second adapter segment at a position where the last residue on the 5' end of the second linker hybridizes to a residue on the second adapter segment that is between 1 residue and 5 residues from the 5' end of the miRNA binding segment. In another embodiment, the second linker hybridizes to the second adapter segment at a position where the last residue on the 5' end of the second linker hybridizes to a residue on the second adapter segment that is immediately adjacent to the 5' end of the miRNA binding segment. In another embodiment, the method further comprises purifying the complex. In another embodiment, the complex is bound to a solid phase through the first adapter segment or through the second adapter segment or through both the first adapter segment and the second adapter segment, and the method further comprises purifying the complex by removing non-hybridized first linkers, second linkers and any other substances that are not bound to the solid phase. In another embodiment, the method further comprises purifying the ligated first linker-miRNA of interest-second linker that has been dehybridized from the capture probe.

In one embodiment, the first linker, or the second linker, or both the first linker and the second linker comprise nuclease resistant nucleotides, or comprise nucleotides with a phosphothioate backbone that render the first linker, or the second linker, or both the first linker and the second linker resistant to nuclease degradation, and purifying the ligated first linker-miRNA of interest-second linker comprises applying DNAase to a solution containing the ligated first linker-miRNA of interest-second linker to destroy any DNA present in the solution. In another embodiment, purifying the ligated first linker-miRNA of interest-second linker comprises circularizing the ligated first linker-miRNA of interest-second linker.

According to another embodiment, of the present invention, there is provided a method for identifying an miRNA of interest. The method comprises: a) isolating the miRNAs according to the present invention, and b) sequencing the miRNA of interest portion of the strand of the ligated first linker-miRNA of interest-second linker. In one embodiment, sequencing comprises subjecting the strand of the ligated first linker-miRNA of interest-second linker to reverse transcription to produce a double stranded product comprising a first strand of the ligated first linker-miRNA of interest-second linker and a second strand that is the complement of the first strand. In another embodiment, sequencing comprises amplifying the double stranded product to produce amplification products. In another embodiment, sequencing comprises cloning the amplification products and culturing the amplification products.

FIGURES

These and other features, aspects and advantages of the present invention will become better understood with regard to the following description, appended claims, and accompanying figures where:

DESCRIPTION

Figure 1:
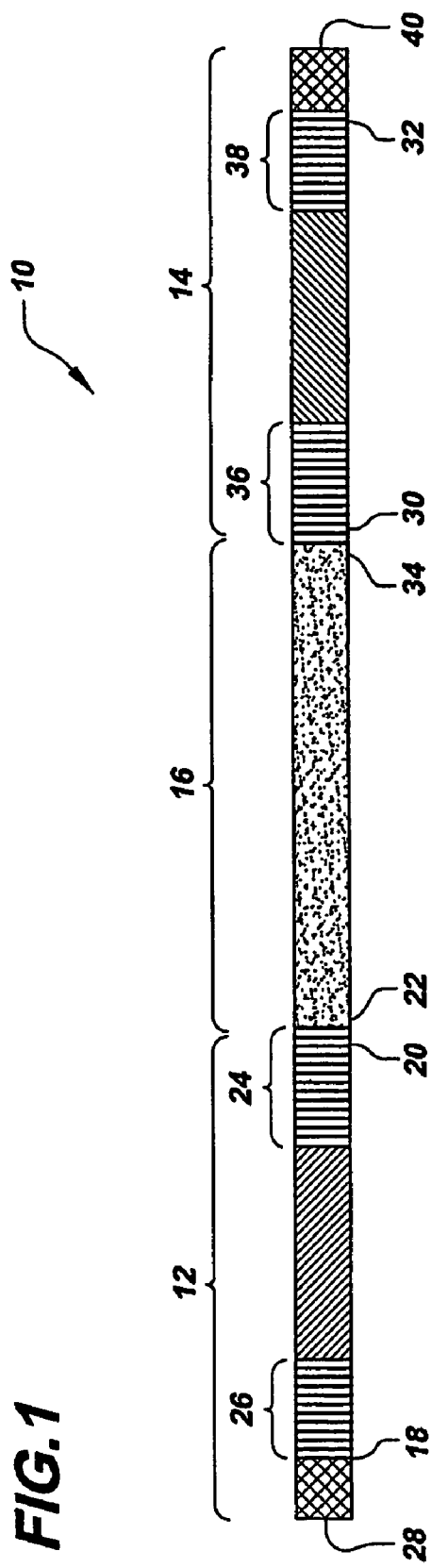
FIG. 1 is a schematic diagram of a capture probe according to the present invention.

According to one embodiment of the present invention, there is provided a method for isolating microRNAs (miRNAs). According to another embodiment of the present invention, there is provided a method for identifying miRNAs. In one embodiment, the method for identifying miRNAs comprises, first, isolating the miRNAs according to the present invention. According to another embodiment of the present invention, there is provided one or more than one capture probe and one or more than one set of capture probes, suitable for use with a method for isolating miRNAs. In one embodiment, the method for isolating miRNAs is a method according to the present invention. The method and capture probes will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, the term "miRNAs" means a naturally occurring, single stranded polyribonucleotide (polyRNA) of between 18 and 24 RNA residues, which is derived from a larger, naturally occurring noncoding eukaryotic precursor RNA (usually having a 'hairpin' configuration)

As used in this disclosure, the terms "one or more than one miRNAs," "an miRNA" and "the miRNA" are intended to be synonymous, that is, are intended to indicate either one miRNA of interest or a plurality of miRNA of interest, except where the context requires otherwise.

As used in this disclosure, the terms "one or more than one capture probe," "a capture probe," "the capture probe" and "the capture probes" are intended to be synonymous, that is, are intended to indicate either one capture probe or a plurality of capture probes, except where the context requires otherwise.

As used in this disclosure, the terms "a first linker," "the first linker" and "the first linkers" are intended to be synonymous, that is, are intended to indicate either one first linker or a plurality of first linkers, except where the context requires otherwise.

As used in this disclosure, the terms "a second linker," "the second linker" and "the second linkers" are intended to be synonymous, that is, are intended to indicate either one second linker or a plurality of second linkers, except where the context requires otherwise.

As used in this disclosure, the term "substantially complementary" and variations of the term, such as "substantial complement," means that at least 90% of all of the consecutive residues in a first strand are complementary to a series of consecutive residues of the same length of a second strand. As will be understood by those with skill in the art with reference to this disclosure, one strand can be shorter than the other strand and still be substantially complementary. With respect to the invention disclosed in this disclosure, for example, the first adapter segment can be shorter than the first linker and still be substantially complementary to the first linker, and the second adapter segment can be shorter than the second linker and still be substantially complementary. The miRNA binding segment can be the same length or longer than the miRNA of interest.

As used in this disclosure, the term "hybridize" and variations of the term, such as "hybridizes" and "hybridized," means a Watson-Crick base pairing of complementary nucleic acid single strands or segments of strands to produce, an anti-parallel, double-stranded nucleic acid, and as used in this disclosure, hybridization should be understood to be between substantially complementary strands unless specified otherwise, or where the context requires otherwise. As an example, hybridization can be accomplished by combining equal molar concentrations of each of the pairs of single strands, such as 100 pmoles, in the presence of 5 ug yeast tRNA in a total volume of 50 µl of aqueous buffer containing 400 mM MOPS, 80 mM DTT, and 40 mM $MgCl_2$ at a pH of 7.3, and then incubating the mixture at 25° C. for one hour while shaking gently.

As used in this disclosure, the term "near the end" and variations of the term, means within 20% of the residues of the identified end residue. For example, near the end of a 20 residue strand, means the first four residues of the identified end of the strand.

According to one embodiment of the present invention, there is provided a capture probe suitable for use with a method for isolating miRNAs according to the present invention. Referring now to FIG. 1, there is shown a schematic diagram of a capture probe 10 according to one embodiment of the present invention. The capture probe 10, and each of its segments, comprises a substance selected from the group consisting of one or more than one type of polynucleotide, including ribonucleotides and deoxynucleotides, one or more than one type of polynucleotide analog, and a combination of one or more than one type of polynucleotide and polynucleotide analog. As can be seen in FIG. 1, the capture probe 10 comprises three segments: a) a first adapter segment 12 having a first adapter segment sequence, b) a second adapter segment 14 having a second adapter segment sequence, and c) an miRNA binding segment 16 having an miRNA binding segment sequence, where the miRNA binding segment 16 is between the first adapter segment 12 and the second adapter segment 14.

According to one embodiment of the present invention, there is provided a set of capture probes comprising at least one capture probe comprising an miRNA binding segment that is substantially complementary to, and capable of hybridizing to, each miRNA listed in a single public database.

According to one embodiment of the present invention, there is provided a plurality of capture probes, where each capture probe of the plurality of capture probes comprises identical first adapter segment sequences, where each capture probe of the plurality of capture probes comprises identical miRNA binding segment sequences, and where each capture probe of the plurality of capture probes comprises identical second adapter segment sequences.

According to one embodiment of the present invention, there is provided a set of capture probes comprising a first capture probe and a second capture probe, where the first capture probe and the second capture probe have identical first adapter segment sequences, where the first capture probe and the second capture probe have identical miRNA binding segment sequences, and where the first capture probe has a second adapter segment sequence that is different from the second adapter segment sequence of the second capture probe.

According to one embodiment of the present invention, there is provided a set of capture probes comprising a first capture probe and a second capture probe, where the first capture probe and the second capture probe have identical first adapter segment sequences, where the first capture probe and the second capture probe have identical second adapter segment sequences, and where the first capture probe has an miRNA binding segment sequence that is different from the miRNA binding segment sequence of the second capture probe.

According to one embodiment of the present invention, there is provided a set of capture probes comprising a first capture probe and a second capture probe, where the first capture probe and the second capture probe have identical miRNA binding segment sequences, where the first capture probe and the second capture probe have identical second adapter segment sequences, and where the first capture probe has a first adapter segment sequence that is different from the first adapter segment sequence of the second capture probe.

According to one embodiment of the present invention, there is provided a set of capture probes comprising a first capture probe and a second capture probe, where the first capture probe and the second capture probe have identical first adapter segment sequences, and where the first capture probe has an miRNA binding segment sequence that is different from the miRNA binding segment sequence of the second capture probe, and where the first capture probe has a second adapter segment sequence that is different from the second adapter segment sequence of the second capture probe.

According to one embodiment of the present invention, there is provided a set of capture probes comprising a first capture probe and a second capture probe, where the first capture probe and the second capture probe have identical miRNA binding segment sequences, where the first capture probe has a first adapter segment sequence that is different from the first adapter segment sequence of the second capture probe, and where the first capture probe has a second adapter segment sequence that is different from the second adapter segment sequence of the second capture probe.

According to one embodiment of the present invention, there is provided a set of capture probes comprising a first capture probe and a second capture probe, where the first capture probe and the second capture probe have identical second adapter segment sequences, where the first capture probe has a first adapter segment sequence that is different from the first adapter segment sequence of the second capture probe, and where the first capture probe has an miRNA binding segment sequence that is different from the miRNA binding segment sequence of the second capture probe.

According to one embodiment of the present invention, there is provided a set of capture probes comprising a first capture probe and a second capture probe, where the first capture probe has a first adapter segment sequence that is different from the first adapter segment sequence of the second capture probe, where the first capture probe has an miRNA binding segment sequence that is different from the miRNA binding segment sequence of the second capture probe, and where the first capture probe has a second adapter segment sequence that is different from the second adapter segment sequence of the second capture probe.

Referring again to FIG. 1, the first adapter segment 12 comprises a 3' end 18 and a 5' end 20. As can be seen in FIG. 1, the 5' end 20 of the first adapter segment 12 is connected to the 3' end 22 of the miRNA binding segment 16, that is the first adapter segment 12 is connected upstream of the miRNA binding segment 16. In one embodiment, the first adapter segment 12 is substantially complementary to and capable of hybridizing a first linker probe designated in this disclosure as a "first linker." When used in the method of the present invention, the first adapter segment 12 facilitates the ligation of the 3' end of the first linker to the 5' end of the miRNA of interest by aligning the first linker in position for ligation to the miRNA of interest.

In one embodiment, the first adapter segment has a number of residues between 5 and 50. In another embodiment, the first adapter segment has a number of residues between 5 and 20. In another embodiment, the first adapter segment has a number of residues between 6 and 16.

In one embodiment, the first adapter segment 12 comprises one or more than one sequence 24 or sequence 26 that is a restriction site motif. In a particularly preferred embodiment, the specific restriction site motif, when present, is not present in the DNA analog of the miRNA of interest that is being isolated and identified by the present method. In one embodiment, the restriction site motif is acted upon by a restriction enzyme selected from the group consisting of BamH I, Hind III and EcoR I. In a preferred embodiment, the restriction site motif is acted upon by a restriction enzyme selected from the group consisting of Not I, Xho I, Xma I and Nhe I, because BamH I, Hind III and EcoR I also act upon some sequences of miRNA. As will be understood by those with skill in the art with reference to this disclosure, however, other suitable restriction site motifs can also be used.

In another embodiment, the first adapter segment 12 comprises a sequence 24 or a sequence 26 that is a polynucleotide synthesis promoter motif for a polynucleotide polymerase, or that is complementary to a polynucleotide synthesis promoter motif for a polynucleotide polymerase. In a preferred embodiment, the polynucleotide synthesis promoter motif is a motif for a polynucleotide synthesis promoter selected from the group consisting of T7, SP6, a T3 DNA dependent RNA polymerase, a type 2 RNA polymerase of E. coli and single stranded DNA dependent N4 RNA polymerase. The polynucleotide synthesis promoter motif can be a motif for any other suitable polynucleotide synthesis promoter, however, as will be understood by those with skill in the art with reference to this disclosure.

As will be understood by those with skill in the art with reference to this disclosure, the sequence that is a restriction site motif of the first adapter segment 12 can be in either position 24 or in the position 26 as indicated in FIG. 1, and the sequence that is a polynucleotide synthesis promoter motif can be in either position 24 or in the position 26 as indicated in FIG. 1. In a preferred embodiment, there is no other a restriction site motif sequence of the first adapter segment 12 other than in the position 24 or in the position 26 as shown in FIG. 1.

In another embodiment, the first adapter segment 12 comprises a solid phase binding group 28 to immobilize the capture probe 10 to a solid phase. In one embodiment, the solid phase binding group 28 is at or near the 3' end 18 of the first adapter segment 12, however, as will be understood by those with skill in the art with reference to this disclosure, the solid phase binding group 28 can be anywhere on the capture probe 10 other than at or near the 3' end 18 of the first adapter segment 12. In one embodiment, the solid phase binding group 28 immobilizes the capture probe 10 to a solid phase covalently. In another embodiment, the solid phase binding group 28 immobilizes the capture probe 10 to a solid phase non-covalently. In one embodiment, the solid phase binding group 28 immobilizes the capture probe 10 to a solid phase reversibly. As used in this context, "reversibly" means that the solid phase binding group 28 immobilizes the capture probe 10 to a solid phase in such a way that the solid phase binding group 28 can be disassociated from the solid phase without destruction of the capture probe 10 and without disruption of hybridization between the capture probe 10 and the ligated first linker 48-miRNA of interest 42-second linker 50 (as disclosed below). In another embodiment, the solid phase binding group 28 immobilizes the capture probe 10 to a solid phase non-reversibly. For example, in one embodiment, the solid phase binding group 28 immobilizes the capture probe 10 to a solid phase non-covalently and reversibly, where the solid phase binding group 28 comprises biotin or an analog of biotin capable of binding with avidin or streptavidin or functional analogs of avidin or streptavidin with high affinity, such as with an affinity having an affinity constant of between about $10^{e12}$ and $10^{e20}$. Additionally for example, in one embodiment the solid phase binding group 28 of the first adapter segment 12 immobilizes the capture probe 10 to a solid phase covalently and non-reversibly, where the solid phase binding group 28 comprises a terminal 5' primary amino group at the 3' end 18 of the first adapter segment 12 for coupling to a solid phase surface having free carboxyl groups using standard carbodiimide chemistry, as will be understood by those with skill in the art with reference to this disclosure. Further, as will be understood by those with skill in the art with reference to this disclosure, any solid phase binding group 28 present in the first adapter segment 12, and any technique for coupling the solid phase binding group 28 to a solid phase used in connection with the present method should not interfere with the hybridization and capture of the miRNA of interest to the miRNA binding segment 16, or with any other step of the present method.

By way of example only, in one embodiment the first adapter segment 12 comprises DNA and has a first adapter segment sequence in the 5' to 3' direction of ATTTAGGTGA-CACTATAG, SEQ ID NO:1.

The second adapter segment 14 comprises a 3' end 30 and a 5' end 32. As can be seen in FIG. 1, the 3' end 30 of the second adapter segment 14 is connected to the 5' end 34 of the miRNA binding segment 16, that is the second adapter segment 14 is connected downstream of the miRNA binding segment 16. In one embodiment, the second adapter segment 14 is substantially complementary to and capable of hybridizing a second linker probe designated in this disclosure as a "second linker." When used in the method of the present invention, the second adapter segment 14 facilitates the ligation of the 5' end of the second linker to the 3' end of the miRNA of interest by aligning the second linker in position for ligation to the miRNA of interest.

In one embodiment, the second adapter segment 14 has a number of residues between 5 and 50. In another embodiment, the second adapter segment 14 has a number of residues between 5 and 20. In another embodiment, the second adapter segment 14 has a number of residues between 6 and 16.

In another embodiment, the second adapter segment 14 comprises one or more than one sequence 36 that is a restriction site motif. In a particularly preferred embodiment, the specific restriction site motif, when present, is not present in the DNA analog of the miRNA of interest that is being isolated and identified by the present methods. In one embodiment, the restriction site motif is acted upon by a restriction enzyme selected from the group consisting of BamH I, Hind III and EcoR I. In a preferred embodiment, the restriction site motif is acted upon by a restriction enzyme selected from the group consisting of Not I, Xho I, Xma I and Nhe I, because BamH I, Hind III and EcoR I also act upon some sequences of miRNA. As will be understood by those with skill in the art with reference to this disclosure, however, other suitable restriction site motifs can also be used.

In one embodiment, the one or more than one sequence 24 that is a restriction site motif is identical to the one or more than one sequence 36 that is a restriction site motif. In another embodiment, the one or more than one sequence 24 that is a restriction site motif is different from the one or more than one sequence 36 that is a restriction site motif.

In one embodiment, the second adapter segment 14 comprises a sequence 38 that is a polynucleotide synthesis promoter motif for a polynucleotide polymerase, or that is complementary to a polynucleotide synthesis promoter motif for a polynucleotide polymerase. In a preferred embodiment, the polynucleotide synthesis promoter motif is a motif for a polynucleotide synthesis promoter selected from the group consisting of T7, SP6, a T3 DNA dependent RNA polymerase, a type 2 RNA polymerase of *E. coli* and single stranded DNA dependent N4 RNA polymerase. The polynucleotide synthesis promoter motif can be a motif for any other suitable polynucleotide synthesis promoter, however, as will be understood by those with skill in the art with reference to this disclosure.

As will be understood by those with skill in the art with reference to this disclosure, the sequence that is a restriction site motif of the second adapter segment 14 can be in either position 36 or in the position 38 as indicated in FIG. 1, and the sequence that is a polynucleotide synthesis promoter motif can be in either position 36 or in the position 38 as indicated in FIG. 1. In a preferred embodiment, there is no other a restriction site motif sequence of the second adapter segment 14 other than in the position 36 or in the position 38 as shown in FIG. 1.

By way of example only, in one embodiment the second adapter segment 14 comprises DNA and has a second adapter segment sequence in the 5' to 3' direction of CCCTATAGT-GAGTCGTATTA SEQ ID NO:2.

In another embodiment, the second adapter segment 14 comprises a solid phase binding group 40 to immobilize the capture probe 10 to a solid phase. In one embodiment, the solid phase binding group 40 is at or near the 5' end 32 of the second adapter segment 14, however, as will be understood by those with skill in the art with reference to this disclosure, the solid phase binding group 40 can be anywhere on the capture probe 10 other than at or near the 5' end 32 of the second adapter segment 14. In one embodiment, the solid phase binding group 40 immobilizes the capture probe 10 to a solid phase covalently. In another embodiment, the solid phase binding group 40 immobilizes the capture probe 10 to a solid phase non-covalently. In one embodiment, the solid phase binding group 40 immobilizes the capture probe 10 to a solid phase reversibly. As used in this context, "reversibly" means that the solid phase binding group 40 immobilizes the capture probe 10 to a solid phase in such a way that the solid phase binding group 40 can be disassociated from the solid phase without destruction of the capture probe 10 and without disruption of hybridization between the capture probe 10 and the ligated first linker 48-miRNA of interest 42-second linker 50 (as disclosed below). In another embodiment, the solid phase binding group 40 immobilizes the capture probe 10 to a solid phase non-reversibly. For example, in one embodiment, the solid phase binding group 40 immobilizes the capture probe 10 to a solid phase non-covalently and reversibly, where the solid phase binding group 40 comprises biotin or an analog of biotin capable of binding with avidin or streptavidin or functional analogs of avidin or streptavidin with high affinity, such as with an affinity having an affinity constant of between about $10^{e12}$ and $10^{e20}$. Additionally for example, in one embodiment the solid phase binding group 40 of the second adapter segment 14 immobilizes the capture probe 10 to a solid phase covalently and non-reversibly, where the solid phase binding group 40 comprises a terminal 3' primary amino group at the 5' end 32 of the second adapter segment 14 for coupling to a solid phase surface having free carboxyl groups using standard carbodiimide chemistry, as will be understood by those with skill in the art with reference to this disclosure. Further, as will be understood by those with skill in the art with reference to this disclosure, any solid phase binding group 40 present in the second adapter segment 14, and any technique for coupling the solid phase binding group 40 to a solid phase used in connection with the present method should not interfere with the hybridization and capture of the miRNA of interest to the miRNA binding segment 16, or with any other step of the present method.

In another embodiment, both the first adapter segment 12 comprises a solid phase binding group 28, and the second adapter segment 14 comprises a solid phase binding group 40. In another embodiment, both the first adapter segment 12 comprises a solid phase binding group 28 at or near the 3' end 18 of the first adapter segment 12, and the second adapter segment 14 comprises a solid phase binding group 40 at or near the 5' end 32 of the second adapter segment 14.

Referring again to FIG. 1 and as stated above, the capture probe 10 of the present invention farther comprises an miRNA binding segment 16. The miRNA binding segment 16 has an miRNA binding segment sequence comprising a 3' end 22 and a 5' end 34, and consists of one or more than one type of polynucleotide, including ribonucleotides and deoxynucleotides, or one or more than one type of polynucleotide analog, or a combination of one or more than one type of polynucleotide and polynucleotide analog. The 3' end 22 of the miRNA binding segment 16 is connected to the 5' end 20 of the first adapter segment 12 of the capture probe 10 according to the present invention, that is, the first adapter segment 12 is connected upstream of the miRNA binding segment 16. The 5' end 34 of the miRNA binding segment 16 is connected to the 3' end 30 of the second adapter segment 14 of the capture probe 10 according to the present invention, that is, the second adapter segment 14 is connected downstream of the miRNA binding segment 16.

In one embodiment, the miRNA binding segment consists of between 18 and 24 DNA residues. In another embodiment, the miRNA binding segment 16 consists of 18 or 19 or 20 or 21 or 22 or 23 or 24 residues selected from the group consisting of DNA, RNA, chimeric DNA/RNA; DNA analogs and RNA analogs.

The miRNA binding segment 16 is substantially complementary to, and capable of hybridizing to, one or more than one miRNA of interest by Watson-Crick base pairing, including an miRNA of interest having a predetermined sequence or having a predetermined size, from a sample. In one embodiment, the sample comprises substances that are chemically related, such as for example, a mixture of messenger RNAs, transfer RNAs, ribosomal RNAs and genomic DNA. An miRNA of interest can be selected from any known miRNAs from any suitable source, as will be understood by those with skill in the art with reference to this disclosure. In one embodiment, the miRNA of interest is selected from a public database. In a preferred embodiment, the central repository provided is the Sanger Institute http://microrna.sanger.ac.uk/ sequences/ to which newly discovered and previously known miRNA sequences can be submitted for naming and nomenclature assignment, as well as placement of the sequences in a database for archiving and for online retrieval via the world wide web. Generally, the data collected on the sequences of miRNAs by the Sanger Institute include species, source, corresponding genomic sequences and genomic location (usually chromosomal coordinates), as well as full length transcription products and sequences for the mature fully processed miRNA (miRNA with a 5' terminal phosphate group).

To select the sequence or sequences of the miRNA binding segment 16, an miRNA of interest, or set of miRNAs of interest is selected from a suitable source, such as for example, the Sanger Institute database or other suitable database, as will be understood by those with skill in the art with reference to this disclosure. If a set of miRNAs of interest is selected from one or more than one source that contains duplicate entries for one or more than one miRNA, in a preferred embodiment, the duplicated entries are first removed so that the set of sequences of miRNAs of interest contains only one sequence for each miRNA of interest. In one embodiment, the set of miRNAs of interest consists of one of each miRNA from a single source or database, including a public source or public database, such as one of each miRNA listed in the central repository provided by the Sanger Institute.

In another embodiment the miRNA of interest is a eucaryotic miRNA. In another embodiment the miRNA of interest is a primate miRNA. In a preferred embodiment, the miRNA of interest is a human miRNA. In another embodiment, the miRNAs in the set of miRNAs of interest are all eucaryotic miRNAs. In another embodiment, the miRNAs in the set of miRNAs of interest are all primate miRNAs. In another embodiment, the miRNAs in the set of miRNAs of interest are all human miRNAs.

Next, the miRNA binding segment is selected to be the substantial complement of the miRNA of interest sequence. In a preferred embodiment, the miRNA binding segment is the exact complement to the miRNA of interest in both length and sequence. In another embodiment, the miRNA binding segment is more than 90% complementary to a segment of the miRNA of interest of the same length as the miRNA of interest sequence. In another embodiment, the miRNA binding segment is more than 80% complementary to a segment of the miRNA of interest of the same length as the miRNA of interest sequence.

In one embodiment, the miRNA binding segment 16 consists of RNA. In one embodiment, the miRNA binding segment 16 consists of DNA. In one embodiment, the miRNA binding segment 16 consists of polynucleotide analogs. In one embodiment, the miRNA binding segment 16 consists of a chimera of more than one polynucleotide or polynucleotide analog selected from the group consisting of RNA, DNA, polynucleotide analogs of RNA, and polynucleotide analogs of DNA. Once, the miRNA binding segment sequence is selected, the miRNA binding segment 16 is synthesized according to standard synthesis techniques known to those with skill in the art, as will be understood by those with skill in the art with reference to this disclosure.

Table I provides a list of ten sample miRNA binding segments 16 which consist of DNA along with the miRNAs that are the exact complement of the miRNA binding segments. As will be understood by those with skill in the art with reference to this disclosure, and as disclosed in this disclosure, this is a sample list of miRNA binding segments 16, and any other sequence serving the function of the miRNA binding segments will also be useful, including for example miRNA binding segments 16 that are the RNA of the miRNA binding segments 16 listed in Table I.

TABLE I

| SEQ ID NO: | miRNA binding segment sequence 5'-3' | miRNA that is complementary to miRNA binding segment |
|---|---|---|
| SEQ ID NO: 3 | AACTATACAACCTACTACCTCA | hsa-let-7a |
| SEQ ID NO: 4 | AACCACACAACCTACTACCTCA | hsa-let-7b |
| SEQ ID NO: 5 | AACCATACAACCTACTACCTCA | hsa-let-7c |
| SEQ ID NO: 6 | ACTATGCAACCTACTACCTCT | hsa-let-7d |
| SEQ ID NO: 7 | ACTATACAACCTCCTACCTCA | hsa-let-7e |
| SEQ ID NO: 8 | AACTATACAATCTACTACCTCA | hsa-let-7f |
| SEQ ID NO: 9 | ACTGTACAAACTACTACCTCA | hsa-let-7g |
| SEQ ID NO: 10 | ACAGCACAAACTACTACCTCA | hsa-let-7i |
| SEQ ID NO: 11 | CACAAGTTCGGATCTACGGGTT | hsa-miR-100 |
| SEQ ID NO: 12 | CTTCAGTTATCACAGTACTGTA | hsa-miR-101 |

Therefore, by way of example only, a capture probe 10 according to the present invention for use in a method for isolating miRNA hsa-let-7a, can have the following sequence in the 5' to 3' direction:

SEQ ID NO: 13
ATTTAGGTGACACTATAGAAACTATACAACCTACTACCTCACCCTATAGT

GAGTCGTATTA, .

According to one embodiment of the present invention, there is a set of capture probes 10 suitable for use with a method for isolating miRNAs. Referring now to Table II, in one embodiment, by way of example, the set consists of at least seven capture probes 10 according to the present invention, where each capture probe 10 has a first adapter segment 12 ATTTAGGTGACACTATAG, SEQ ID NO:1, a second adapter segment 14 of CCCTATAGTGAGTCGTATTA SEQ ID NO:2, and an miRNA binding segment 16 varying from 18 mer to 24 mer, and having a nucleotide or nucleotide analog (N) (such as for example A, G, C, T as ribonucleotides or deoxynucleotides) capable of hybridizing with a nucleotide on an miRNA. In a preferred embodiment, as shown, the 5' end 32 of the second adapter segment 14 is biotinylated to bind to a solid phase.

TABLE II

| SEQ ID NO: | Capture Probe Sequence 5'-3' | Size of miRNA Captured |
|---|---|---|
| SEQ ID NO: 14 | 5'biotin-ATTTAGGTGACAC TATAGNNNNNNNNNNNNNNNNNN NCCCTATAGTGAGTCGTATTA | 18 mer |
| SEQ ID NO: 15 | 5'biotin-ATTTAGGTGACAC TATAGNNNNNNNNNNNNNNNNNN NNCCCTATAGTGAGTCGTATTA | 19 mer |
| SEQ ID NO: 16 | 5'biotin-ATTTAGGTGACAC TATAGNNNNNNNNNNNNNNNNNN NNNCCCTATAGTGAGTCGTATT A | 20 mer |

TABLE II-continued

| SEQ ID NO: | Capture Probe Sequence 5'-3' | Size of miRNA Captured |
|---|---|---|
| SEQ ID NO: 17 | 5'biotin-ATTTAGGTGACAC TATAGNNNNNNNNNNNNNNNNNN NNNNCCCTATAGTGAGTCGTAT TA | 21 mer |
| SEQ ID NO: 18 | 5'biotin-ATTTAGGTGACAC TATAGNNNNNNNNNNNNNNNNNN NNNNNCCCTATAGTGAGTCGTA TTA | 22 mer |
| SEQ ID NO: 19 | 5'biotin-ATTTAGGTGACAC TATAGNNNNNNNNNNNNNNNNNN NNNNNNCCCTATAGTGAGTCGT ATTA | 23 mer |
| SEQ ID NO: 20 | 5'biotin-ATTTAGGTGACAG TATAGNNNNNNNNNNNNNNNNNN NNNNNNNCCCTATAGTGAGTCG TATTA | 24 mer |

The capture probe 10 of the present invention can be synthesized according to standard techniques, as will be understood by those with skill in the art with reference to this disclosure. In one embodiment, the capture probe 10 is synthesized as a contiguous single sequence for each miRNA of interest to be isolated and detected. In a preferred embodiment, there is provided a set of capture probes 10 comprising a first capture probe and a second capture probe that are synthesized separately, where the sequence of the first capture probe has one or more than one difference with the sequence of the second capture probe, and where the set of capture probes 10 is produced by mixing the first capture probe and the second capture probe after they are synthesized.

In one embodiment, the capture probes 10 are synthesized by combining the sequence text strings for the first adapter segment 12, the miRNA binding segment 16, and the second adapter segment 14 in a database or spreadsheet to generate a capture probe 10 sequence, and then synthesizing the capture probe 10 according to standard techniques, as will be understood by those with skill in the art with reference to this disclosure. In one embodiment, the capture probes 10 are designed for use in a method according to the present invention, and then purchased from a vendor of polynucleotide or polynucleotide analog sequences, such as for example, from Integrated DNA Technologies (Coralville, Iowa US) or Invitrogen Corp. (Carlsbad, Calif. US).

According to another embodiment of the present invention, there is provided a method for isolating an miRNA (microRNA) of interest from a sample comprising the miRNA of interest. According to another embodiment of the present invention, there is provided a method for identifying miRNAs. In one embodiment, the method for identifying miRNAs comprises, first, isolating the miRNAs according to the present invention. Referring now to FIG. 2 through FIG. 6, there are shown some of the steps in certain embodiments of the methods. The steps shown are not intended to be limiting nor are they intended to indicate that each step depicted is essential to the method, but instead are exemplary steps only.

As can be seen, the method comprises, first, providing a sample comprising an miRNA of interest 42. In one embodiment, the sample further comprises one or more than one substance that is chemically related to the miRNA of interest 42, such as for example, a substance selected from the group consisting of messenger RNA, transfer RNA, ribosomal RNA, siRNA, 5S/5.8SrRNA, genomic DNA and a combination of the preceding. In one embodiment, the sample further comprises one or more than one RNA other than miRNA, such as for example, a substance selected from the group consisting of messenger RNA, transfer RNA, ribosomal RNA, siRNA, 5S/5.8SrRNA and a combination of the preceding. All of the RNA in the sample, regardless of the type of RNA, constitutes the "total RNA" in the sample.

In one embodiment, the sample is from a eukaryote. In another embodiment, the sample is from a primate. In a preferred embodiment, the sample is from a human.

In one embodiment, the sample comprises a tissue or fluid selected from the group consisting of blood, brain, heart, intestine, liver, lung, pancreas, muscle, a leaf, a flower, a plant root and a plant stem.

The miRNA of interest 42 has an miRNA of interest sequence, and comprises 3' end 44 and a 5' end 46. In one embodiment, the miRNA of interest consists of between 18 and 24 RNA residues. In another embodiment, the miRNA of interest consists of 18 or 19 or 20 or 21 or 22 or 23 or 24 RNA residues.

The miRNA of interest 42 is substantially complementary to, and capable of hybridizing to, an miRNA binding segment 16 of a capture probe 10 according to the present invention by Watson-Crick base pairing. In one embodiment, the miRNA of interest 42 is listed in a public database. In a preferred embodiment, the public database is a central repository provided by the Sanger Institute http://microrna.sanger.ac.uk/sequences/ to which miRNA sequences are submitted for naming and nomenclature assignment, as well as placement of the sequences in a database for archiving and for online retrieval via the world wide web. Generally, the data collected on the sequences of miRNAs by the Sanger Institute include species, source, corresponding genomic sequences and genomic location (chromosomal coordinates), as well as full length transcription products and sequences for the mature fully processed miRNA (miRNA with a 5' terminal phosphate group).

In one embodiment, the sample provided comprises a plurality of miRNAs of interest 42, where each of the plurality of miRNAs of interest 42 has miRNA of interest sequences that are identical to one another. In one embodiment, the sample provided comprises a plurality of miRNAs of interest 42, where at least two of the plurality of miRNAs of interest 42 have miRNA of interest sequences that are different from one another. In one embodiment, the sample provided comprises a plurality of miRNAs of interest 42 comprising a first miRNA of interest having a first miRNA of interest sequence, and a second miRNA of interest having a second miRNA of interest sequence, where the first miRNA of interest sequence is different from the second miRNA of interest sequence. In another embodiment, the sample provided comprises a plurality of miRNAs of interest 42 comprising a first miRNA of interest having a first miRNA of interest sequence, a second miRNA of interest having a second miRNA of interest sequence, and a third miRNA of interest having a third miRNA of interest sequence, where the first miRNA of interest sequence is different from the second miRNA of interest sequence, where the first miRNA of interest sequence is different from the third miRNA of interest sequence, and where second miRNA of interest sequence is different from the third miRNA of interest sequence.

In one embodiment, the method further comprises isolating the total RNA from the sample after providing the sample. In one embodiment, isolating the total RNA is accomplished according to techniques well known to those with skill in the art, such as for example using a commercially available kit for the isolation of total RNA available from Ambion, Inc. (Austin, Tex. US), Invitrogen Corp. and Qiagen, Inc. (Valencia, Calif. US), among others, as will be understood by those with skill in the art with reference to this disclosure. As will be understood by those with skill in the art with reference to this disclosure, when the method comprises isolating the total RNA from the sample after providing the sample, the term "sample" means the isolated total RNA for the remaining steps in the method.

Next, the method further comprises providing a capture probe 10. In one embodiment, the capture probe 10 provided is a capture probe 10 according to the present invention. When the capture probe 10 is a capture probe 10 according to the present invention, in all respects, the capture probe 10 provided has the characteristics and attributes as disclosed for a capture probe 10 according to the present invention, some of which will be repeated hereafter for clarity. The capture probe 10 has a capture probe sequence, and comprises three segments: a) a first adapter segment 12 having a first adapter segment sequence, and comprising a 3' end 18 and a 5' end 20; b) a second adapter segment 14 having a second adapter segment sequence, and comprising a 3' end 30 and a 5' end 32; and c) an miRNA binding segment 16 having an miRNA binding segment sequence, and comprising a 3' end 22 and a 5' end 34, where the 5' end 20 of the first adapter segment 12 is connected to the 3' end 22 of the miRNA binding segment 16, and where the 5' end of the miRNA binding segment 34 is connected to the 3' end 30 of the second adapter segment 14. The specificity of the miRNA binding segment 16 to the miRNA of interest 42 allows the method to be used directly on a sample containing substances related to miRNA or on isolated total RNA without requiring the specific separation of miRNAs from the sample or from the total RNA, such as for example by either gel purification or chromatographic purification, as necessary in prior art methods.

In one embodiment, the capture probe 10 provided is a set of capture probes, where each of the set of capture probes provided have capture probe sequences that are identical to one another. In one embodiment, the capture probe 10 provided is a set of capture probes, where at least two capture probes of the set of capture probes have capture probe sequences that are different from one another. In another embodiment, the capture probe 10 is a set of capture probes comprising a first capture probe having a first capture probe sequence, and a second capture probe having a second capture probe sequence, where the first capture probe sequence is different from the second capture probe sequence. In another embodiment, the capture probe 10 provided is a set of capture probes comprising a first capture probe having a first capture probe sequence, a second capture probe having a second capture probe sequence, and a third capture probe having a third capture probe sequence, where the first capture probe sequence is different from the second capture probe sequence, where the first capture probe sequence is different from the third capture probe sequence, and where second capture probe sequence is different from the third capture probe sequence.

Then, the method comprises providing a first linker 48 and a second linker 50. In one embodiment, the first linker segment and the second linker segment comprise a substance selected from the group consisting of one or more than one type of polynucleotide, including ribonucleotides and deoxynucleotides, one or more than one type of polynucleotide analog, and a combination of one or more than one type of polynucleotide and polynucleotide analog. In one embodiment, the first linker 48, or the second linker 50, or both the first linker 48 and the second linker 50 are resistant to nuclease degradation. In a preferred embodiment, the first linker 48, or the second linker 50, or both the first linker 48 and the second linker 50 comprise nuclease resistant nucleotides. In another preferred embodiment, the first linker 48, or the second linker 50, or both the first linker 48 and the second linker 50 comprise nucleotides with a phosphothioate backbone that render the first linker 48, or the second linker 50, or both the first linker 48 and the second linker 50 resistant to nuclease degradation. In another preferred embodiment, the first linker 48, or the second linker 50, or both the first linker 48 and the second linker 50 comprise both nuclease resistant nucleotides and nucleotides with a phosphothioate backbone that render the first linker 48, or the second linker 50, or both the first linker 48 and the second linker 50 resistant to nuclease degradation.

The first linker 48 has a first linker sequence, and comprises a 3' end 52 and a 5' end 54. The first linker 48 is substantially complementary to, and capable of hybridizing to, the first adapter segment 12 of a capture probe 10 according to the present invention by Watson-Crick base pairing. The second linker 50 has a second linker sequence, and comprises a 3' end 56 and a 5' end 58. The second linker 50 is substantially complementary to, and capable of hybridizing to, the second adapter segment 14 of a capture probe 10 according to the present invention by Watson-Crick base pairing. The first linker 48 and the second linker 50 each comprises between 6 and 50 residues.

In a preferred embodiment, the first linker 48 comprises at least 10 residues, and at least 10 residues at the 3' end 52 of the first linker 48 are exactly the complement of the corresponding residues at or near the 5' end 20 of the first adapter segment 12. In another embodiment, the second linker 50 comprises at least 10 residues, and at least 10 residues at the 5' end 58 of the second linker 50 are exactly the complement of the corresponding residues at or near the 3' end 30 of the second adapter segment 14.

In a preferred embodiment, the 3' end 52 of the first linker 48 is capable of being ligated to the 5' end 46 of the miRNA of interest 42 by a suitable ligase, such as for example T4 polynucleotide ligase, or by another suitable chemical reaction.

In a preferred embodiment, the 5' end 58 of the second linker 50 is a nucleotide with a 5' pyrophosphate bond between it and its adjacent 5' end nucleotide of the second adapter segment 14 to allow ligation of the 5' end 58 of the second linker 50 to the 3' end 44 of the miRNA of interest 42 by a suitable ligase, such as for example T4 polynucleotide ligase, or by another suitable chemical reaction. In a preferred embodiment, the 5' end 58 of the second linker 50 additionally comprises a 5' pyrophosphate adenosine.

In one embodiment, the 5' end 54 of the first linker 48, or the 3' end 56 of the second linker 50, or both the 5' end 54 of the first linker 48 and the 3' end 56 of the second linker 50 comprise a label, such as for example a fluorescent dye, to facilitate detection, as will be understood by those with skill in the art with reference to this disclosure. Further, the first linker 48, or the second linker 50, or both the first linker 48 and the second linker 50 can comprise a label, such as for example a fluorescent dye, to facilitate detection at a position other than at the 5' end 54 of the first linker 48, or the 3' end 56 of the second linker 50, as long as the presence of the label does not interfere with other steps of the present method, as will be understood by those with skill in the art with reference to this disclosure.

In one embodiment, the 5' end 54 of first linker 48 comprises one or more than one residue that extends beyond the 3' end 18 of the first adapter segment 12 after the first linker 48 hybridizes to the first adapter segment 12. In one embodiment, the one or more than one residue of the 5' end 54 of first linker 48 that extends beyond the 3' end 18 of the first adapter segment 12 functions as a primer binding site that allows the first linker 48 to be distinguished from the second linker 50 in downstream amplification reactions. For example, in one embodiment, the first linker 48 comprises, from the 5' end 54 to the 3' end 52 of first linker 48, a T3 promoter sequence, a short spacer sequence and a T7 promoter sequence, while the nucleotide residues of the first adapter segment 12 consist of the substantial complement of the T7 promoter sequence only.

In one embodiment, the 3' end 56 of second linker 50 comprises one or more than one residue that extends beyond the 5' end 20 of the second adapter segment 14 after the second linker 50 hybridizes to the second adapter segment 14. In one embodiment, the one or more than one residue of the 3' end 56 of second linker 50 that extends beyond the 5' end 32 of the second adapter segment 14 functions as a primer binding site that allows the second linker 50 to be distinguished from the first linker 48 in downstream amplification reactions. For example, in one embodiment, the second linker 50 comprises, from the 3' end 56 to the 5' end 58 of second linker 50, a T3 promoter sequence, a short spacer sequence and an SP6 promoter sequence, while the nucleotide residues of the second adapter segment 14 consist of the substantial complement of the SP6 promoter sequence only.

After the first linker sequence of the first linker 48, and the second linker sequence of the second linker 50 are designed, the first linker 48 and the second linker 50 can be synthesized according to standard techniques, as will be understood by those with skill in the art with reference to this disclosure. Alternately, the first linker 48 and the second linker 50 can be purchased from a vendor of polynucleotide or polynucleotide analog sequences, such as for example, from Integrated DNA Technologies or Invitrogen Corp.

Figure 2:
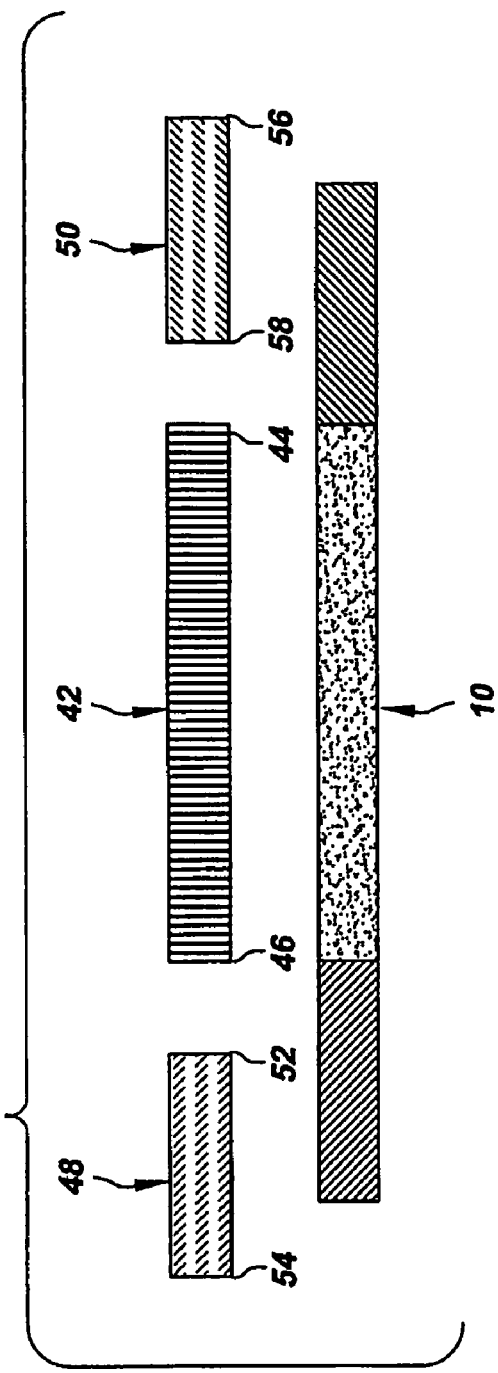
FIG. 2 through FIG. 6 show diagrams of some of the steps in certain embodiments of a method for isolating miRNAs and the method for identifying miRNAs, according to the present invention.

Referring now to FIG. 2, the method then comprises combining the capture probe 10, the first linker segment 48, the second linker segment 50 and the sample, represented in FIG. 2 by the miRNA of interest 42. In a preferred embodiment, the method comprises combining the sample, the capture probe 10, the first linker 48 and the second linker 50 in a solution. The capture probe 10, the first linker 48, the second linker 50 and the sample can be combined simultaneously, or sequentially in any order, as will be understood by those with skill in the art with reference to this disclosure. For example, the capture probe 10 is combined with the sample first, and then the capture probe 10 and sample are combined with the first linker 48 and second linker 50; or alternately for example, the capture probe 10, first linker 48 and second linker 50 are combined first, and then the capture probe 10, first linker 48 and second linker 50 are combined with the sample; or alternately for example, the first linker 48 and the second linker 50 are combined with the sample first, and then the capture probe 10 is combined with the first linker 48, second linker 50 and the sample.

In one embodiment, combining the capture probe 10, the first linker 48, the second linker 50 and the sample comprises combining approximately equimolar amounts of the capture probe 10, the first linker 48 and the second linker 50. In another embodiment, combining the capture probe 10, the first linker 48, the second linker 50 and the sample comprises combining approximately equimolar amounts of the capture probe 10, the first linker 48 and the second linker 50 with an amount of sample expected to contain approximately one tenth the molar amount of miRNA of interest 42 as of the capture probe 10, the first linker 48 and the second linker 50. In another embodiment, combining the capture probe 10, the first linker 48, the second linker 50 and the sample comprises combining approximately equimolar amounts of the capture probe 10, the first linker 48 and the second linker 50 with an amount of sample expected to contain approximately one half and one tenths and the molar amount of miRNA of interest 42 as of the capture probe 10, the first linker 48 and second linker 50. In one embodiment, combining the capture probe 10, the first linker 48, the second linker 50 and the sample comprises combining the sample with between 0.1 pmoles and 100 pmoles/μl each of the capture probe 10, the first linker 48 and the second linker 50 in a suitable buffer to create a solution comprising the capture probe 10, the first linker 48, the second linker 50 and the sample. In a preferred embodiment, the buffer is selected from the group consisting of 1×TE buffer in 0.1-1 M sodium chloride, and 0.1M MOPS in 1 mM EDTA and 100 mM sodium chloride. As will be understood by those with skill in the art with reference to this disclosure, the pH selected for the buffer will be one that optimizes the intended reactions. In general, the pH selected will be between 6 and 8, preferably between 6.4 and 7.4 and more preferably, near 7.0. In a preferred embodiment, the method further comprises adding one or more than one. RNAse inhibitor to the combination of the sample, the capture probe 10, the first linker 48, the second linker 50, such as for example an RNAase inhibitor selected from the group consisting of lithium dodecylsulfate (LiDS), the ammonium salt of tricarboxylic acid and sodium salt of aurine tricarboxylic acid.

Figure 3:
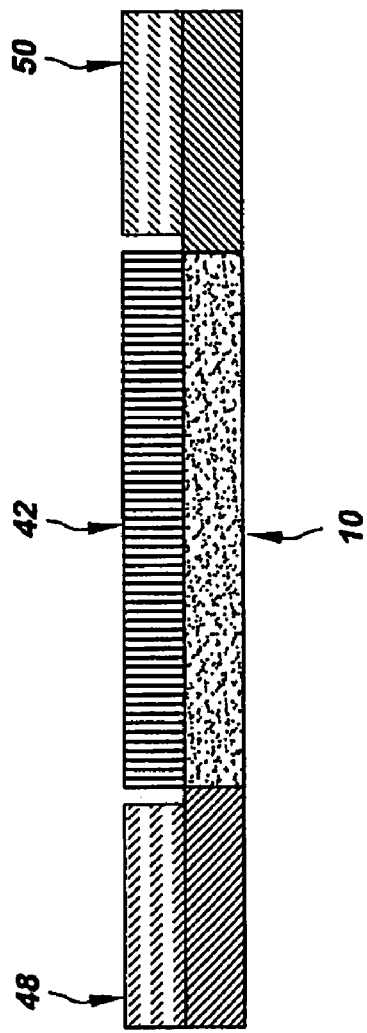

Referring now to FIG. 3, after combining the capture probe 10, the first linker 48, the second linker 50 and the sample, the method comprises allowing the first linker 48 to hybridize with the first adapter segment 12, the miRNA of interest 42 to hybridize with the miRNA binding segment 16, and the second linker 50 to hybridize with the second adapter segment 14, thereby binding the first linker 48, the miRNA of interest 42, and the second linker 50 to the capture probe 10. In one embodiment, allowing the first linker 48 to hybridize with the first adapter segment 12, the miRNA of interest 42 to hybridize with the miRNA binding segment 16, and the second linker 50 to hybridize with the second adapter segment 14 comprises incubating the solution comprising first linker 48, the second linker 50, the capture probe 10 and the sample for between 1 minute and 60 minutes at between 25° C. and 50° C. until substantially all of the miRNA of interest 42 has hybridized to the capture probes 10.

In one embodiment, the first adapter segment 12 comprises a solid phase binding group 28, or the second adapter segment 14 comprises a solid phase binding group 40, or both the first adapter segment 12 comprises a solid phase binding group 28 and the second adapter segment 14 comprises a solid phase binding group 40, as disclosed in this disclosure, and the method further comprises binding the capture probe 10 to a solid phase (not shown) before or after combining the capture probe 10, the first linker 48, the second linker 50 and the sample. In one embodiment, the solid phase is a plurality of beads where each bead has a diameter of between 0.01μ and 5μ, though the solid phase can be any suitable solid phase as will be understood by those with skill in the art with reference to this disclosure. For example, in one embodiment, the solid phase binding group comprises biotin, and the solid phase is paramagnetic particles having a diameter of 1.0μ and comprising streptavidin immobilized to the surface of the particles.

In one embodiment, the capture probes 10 are bound to a solid phase through the first adapter segment 12 or through the second adapter segment 14 or through both the first adapter segment 12 and the second adapter segment 14, and the method further comprises hybridizing the miRNA of interest 42 to the miRNA binding segment 16 of the capture probes 10 bound to the solid phase, and then incubating the capture probes/miRNA of interest-bound to the solid phase with the first linker 48 and second linker 50 under conditions sufficient to hybridize the first linker 48 to the first adapter segment 12 of the capture probe 10 and the second linker 50 to the second adapter segment 14 of the capture probe 10.

In a preferred embodiment, the first linker 48 hybridizes to the first adapter segment 12 at a position where the last residue on the 3' end 52 of the first linker 48 hybridizes to a residue on the first adapter segment 12 that is between 1 residue and 5 residues from the 3' end 22 of the miRNA binding segment 16. In a particularly preferred embodiment, the first linker 48 hybridizes to the first adapter segment 12 at a position where the last residue on the 3' end 52 of the first linker 48 hybridizes to a residue on the first adapter segment 12 that is immediately adjacent to the 3' end 22 of the miRNA binding segment 16.

In a preferred embodiment, the second linker 50 hybridizes to the second adapter segment 14 at a position where the last residue on the 5' end 58 of the second linker 50 hybridizes to a residue on the second adapter segment 14 that is between 1 residue and 5 residues from the 5' end 34 of the miRNA binding segment 16. In a particularly preferred embodiment, the second linker 50 hybridizes to the second adapter segment 14 at a position where the last residue on the 5' end 58 of the second linker 50 hybridizes to a residue on the second adapter segment 14 that is immediately adjacent to the 5' end 34 of the miRNA binding segment 16.

In one embodiment, the capture probe is bound to a solid phase through the first adapter segment 12 or through the second adapter segment 14 or through both the first adapter segment 12 and the second adapter segment 14, and the method further comprises purifying the capture probe 10 with hybridized first linker 48, miRNA of interest 42 and second linker 50-bound to the solid phase by removing non-hybridized first linkers 48, second linkers 50 and any other substances such as messenger RNAs, transfer RNAs, ribosomal RNAs and genomic DNA that are not bound to the solid phase. In one embodiment, purifying comprises washing the capture probe 10 with hybridized first linker 48, miRNA of interest 42 and second linker 50-bound to the solid phase with a suitable buffer, such as for example 1×TE buffer in 0.1-1 M sodium chloride (pH 6.4-7.4, preferably pH 6.8-7.2). In another embodiment, the solid phase comprises paramagnetic particles, the solid phase is contained in a vessel comprising a surface and a cap, and purifying comprises applying a magnetic field to attract the solid phase to the surface of the vessel or the cap of the vessel. In a preferred embodiment, after applying the magnetic field to attract the solid phase to the surface of the vessel or the cap of the vessel, the method comprises washing the capture probe 10 with hybridized first linker 48, miRNA of interest 42 and second linker 50-bound to the solid phase with a suitable buffer, such as for example 0.1×TE buffer (pH 7.4).

Figure 4:
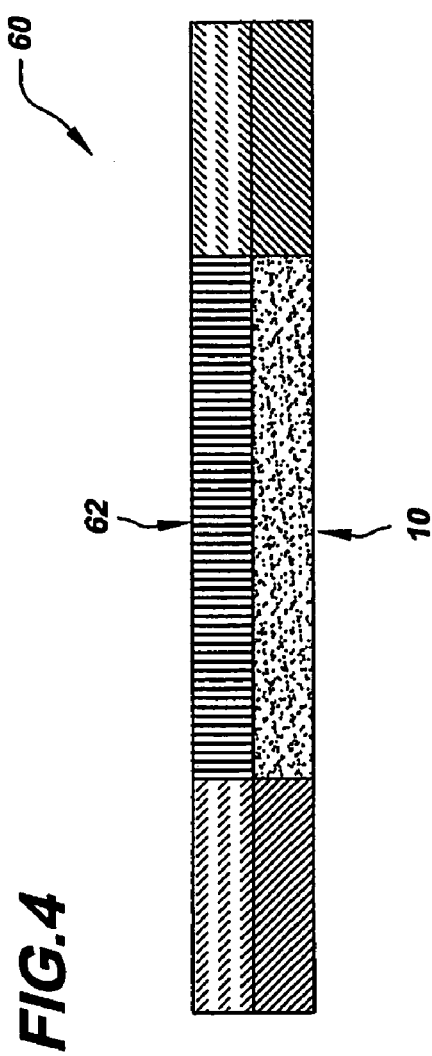

Next, as show in FIG. 4, the method comprises covalently ligating the 3' end 52 of the first linker 48 that is hybridized to the first adapter segment 12 to the 5' end 46 of the miRNA of interest 42 that is hybridized to the miRNA binding segment 16, and then covalently ligating the 3' end 44 of the miRNA of interest 42 that is hybridized to the miRNA binding segment 16 to the 5' end 58 of the second linker 50 that is hybridized to the second adapter segment 14. Ligation of the 3' end 52 of the first linker 48 to the 5' end 46 of the miRNA of interest 42, and ligation of the 3' end 44 of the miRNA of interest 42 to the 5' end 58 of the second linker 50 can be accomplished in any order, including simultaneously or sequentially. In one embodiment, the ligation is accomplished by standard techniques, as will be understood by those with skill in the art with reference to this disclosure. In a preferred embodiment, the ligation comprises treating the capture probe 10 with the hybridized first linker 48, miRNA of interest 42 and second linker 50 with a suitable ligase, such as for example T4 polynucleotide ligase in the presence of suitable buffer and essential cofactors for a sufficient time for the ligation to proceed to near total completion of ligation. As will be understood by those with skill in the art with reference to this disclosure, the presence of the first adapter segment 12 and the second adapter segment 14 in the capture probe 10 facilitate the ligation of the first linker 48 and the second linker 50 to the miRNA of interest 42 by aligning the 3' end 52 of the first linker 48 with the 5' end of the miRNA of interest 42, and aligning the 5' end 58 of the second linker 50 with the 3' end 22 of the miRNA of interest 42. The ligation step produces a "complex 60" defined as a strand 62 of first linker 48, miRNA of interest 42 and second linker 50 that have been ligated together ("ligated first linker 48-miRNA of interest 42-second linker 50"), and where the strand 62 is hybridized to the capture probe 10.

In one embodiment, the method further comprises purifying the complex 60. In a preferred embodiment, purifying comprises washing the complex 60 with a suitable buffer, such as for example T4 polynucleotide ligase incubation buffer containing ATP (Promega Corp., Madison Wis. US)

In one embodiment, the complex 60 is bound to a solid phase through the first adapter segment 12 or through the second adapter segment 14 or through both the first adapter segment 12 and the second adapter segment 14, and the method further comprises purifying the complex 60 by removing non-hybridized first linkers 48, non-hybridized second linkers 50 and any other substances such as messenger RNAs, transfer RNAs, ribosomal RNAs and genomic DNA that are not bound to the solid phase. In one embodiment, purifying comprises washing the complex 60-bound to the solid phase with a suitable buffer, such as for example 0.1×TE buffer (pH 7.4). In another embodiment, the solid phase comprises paramagnetic particles, and purifying comprises applying a magnetic field to attract the complex 60-bound to the solid phase to the vessel containing the complex 60-bound to the solid phase. In a preferred embodiment, after applying the magnetic field, the method comprises washing the complex 60-bound to the solid phase with a suitable buffer, such as for example 0.1×TE buffer (pH 7.4).

Figure 5:
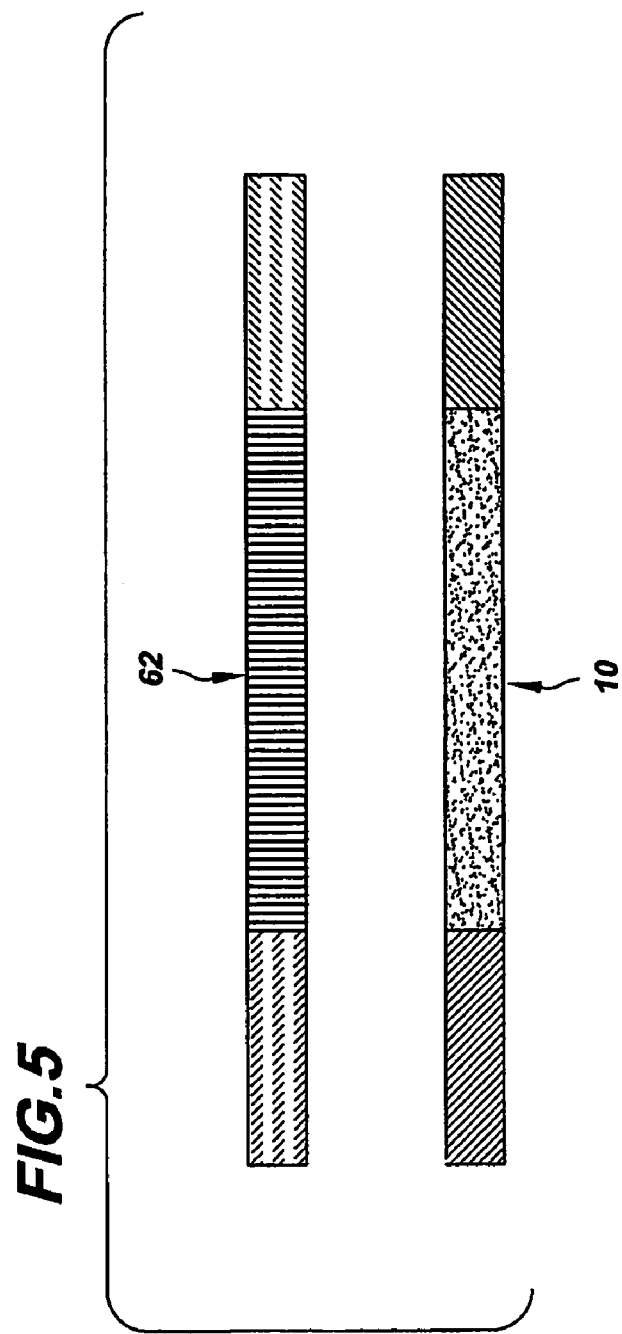

Next, as shown in FIG. 5, the method comprises dehybridizing the strand 62 of the ligated first linker 48-miRNA of interest 42-second linker 50 from the capture probe 10. In one embodiment, dehybridization is accomplished by standard techniques, as will be understood by those with skill in the art with reference to this disclosure. In a preferred embodiment, dehybridizing comprises applying a substance that abolishes or substantially reduces the hybridization between the capture probe 10 and the strand 62 of the ligated first linker 48-miRNA of interest 42-second linker 50. In a preferred embodiment, the complex is bound to the solid phase, and dehybridizing comprises applying a low ionic strength solution to the bound complex, such as for example a solution of sterile nuclease free water warmed to 80° C., thereby producing a solution of the ligated first linker 48-miRNA of interest 42-second linker 50, and of capture probe 10-bound to the solid phase.

In one embodiment, the method further comprises purifying the ligated first linker 48-miRNA of interest 42-second linker 50 that has been dehybridized from the capture probe 10. In one embodiment, purifying the ligated first linker 48-miRNA of interest 42-second linker 50 is accomplished according to standard techniques, as will be understood by those with skill in the art with reference to this disclosure. In a preferred embodiment, the capture probes 10 are bound to a solid phase, and purifying the ligated first linker 48-miRNA of interest 42-second linker 50 comprises separating the ligated first linker 48-miRNA of interest 42-second linker 50 from the capture probes 10-bound to the solid phase by transferring a solution containing the ligated first linker 48-miRNA of interest 42-second linker 50 after dehybridization to a separate container. In another preferred embodiment, the first linker 48, or the second linker 50, or both the first linker 48 and the second linker 50 comprise nuclease resistant nucleotides, or comprise nucleotides with a phosphothioate backbone that render the first linker 48, or the second linker 50, or both the first linker 48 and the second linker 50 resistant to nuclease degradation, and purifying the ligated first linker 48-miRNA of interest 42-second linker 50 comprises applying DNAase to a solution containing the ligated first linker 48-miRNA of interest 42-second linker 50 to destroy any DNA present in the solution, thereby advantageously decreasing false signals during downstream amplification with PCR.

In another preferred embodiment, purifying the ligated first linker 48-miRNA of interest 42-second linker 50 comprises circularizing the ligated first linker 48-miRNA of interest 42-second linker 50. Circularizing the ligated first linker 48-miRNA of interest 42-second linker 50 can be accomplished by standard techniques, as will be understood by those with skill in the art with reference to this disclosure. In one embodiment, circularizing comprises treating the ligated first linker 48-miRNA of interest 42-second linker 50 with a ligase that catalyzes intramolecular ligation (i.e., circularization) of single-stranded polynucleotide templates having a 5'-phosphate and a 3'-hydroxyl group, such as for example CircLigase™ (Epicentre Biotechnologies, Madison, Wis. US). In another embodiment, circularizing comprises treating the ligated first linker 48-miRNA of interest 42-second linker 50 with a polynucleotide kinase, such as for example T4 polynucleotide kinase, to phosphorylate the 5' ends of the ligated first linker 48-miRNA of interest 42-second linker 50 before treating the ligated first linker 48-miRNA of interest 42-second linker 50 with a ligase that catalyzes intramolecular ligation. In one embodiment, the method comprises circularizing the strand 62 of the ligated first linker 48-miRNA of interest 42-second linker 50, and purifying the strand 62 of the ligated first linker 48-miRNA of interest 42-second linker 50 comprises treating the solution containing the circularized strand 62 of the ligated first linker 48-miRNA of interest 42-second linker 50 with one or more than one exonuclease, such as for example exonuclease I from E. coli to destroy any polynucleotides or polynucleotide analogs present in the solution other than the circularized strand 62 of the ligated first linker 48-miRNA of interest 42-second linker 50.

Figure 6:
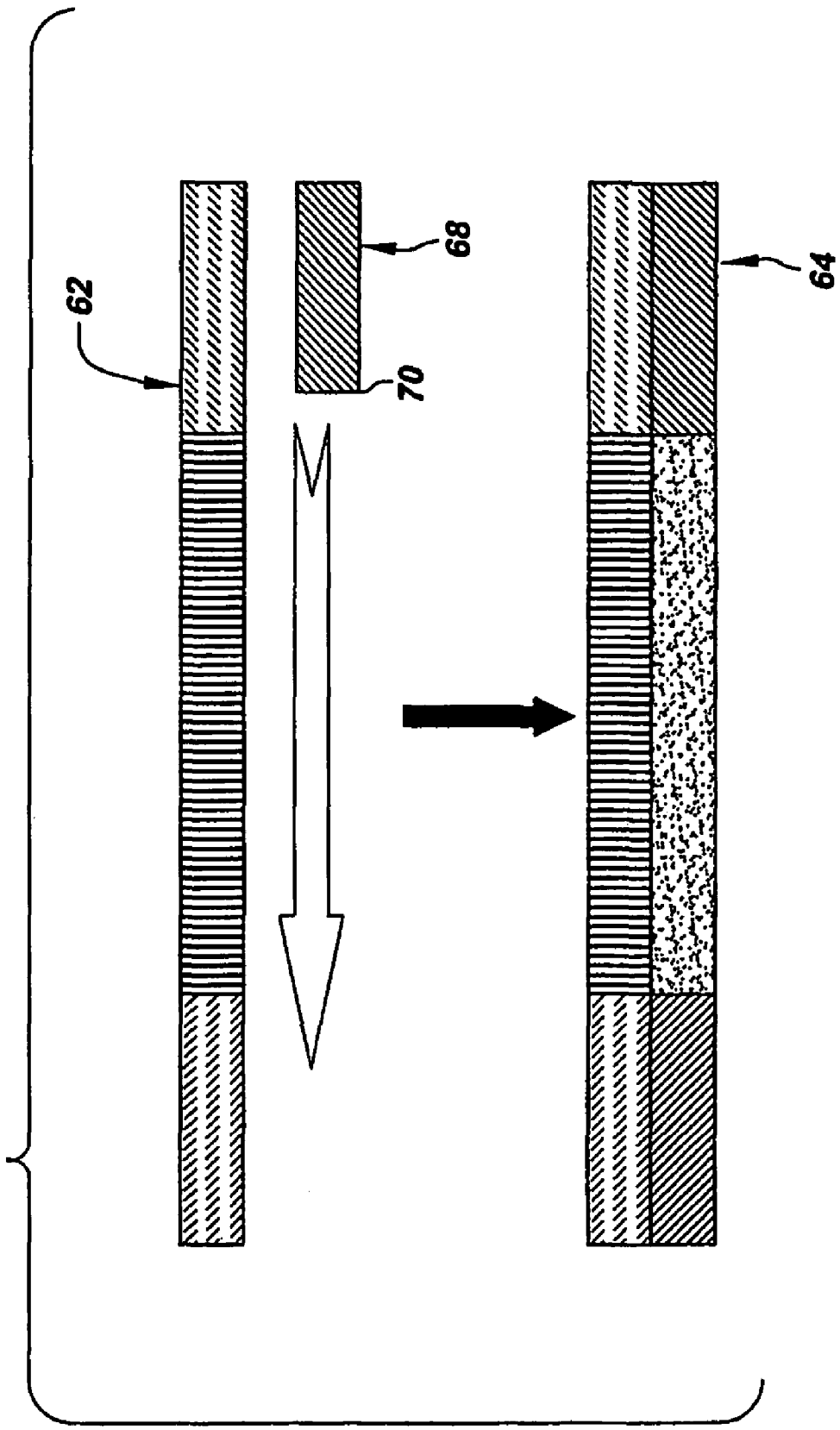

According to another embodiment of the present invention, there is provided a method for identifying an miRNA of interest 42. In one embodiment, the method for identifying an miRNA of interest 42 comprises, first, isolating the miRNA of interest 42 according to the present invention. In one embodiment, the method further comprises sequencing the miRNA of interest 42 portion of the strand 62 of the ligated first linker 48-miRNA of interest 42-second linker 50 by standard techniques, as will be understood by those with skill in the art with reference to this disclosure. In a preferred embodiment, as shown in FIG. 6, sequencing the miRNA of interest 42 of the strand 62 of the ligated first linker 48-miRNA of interest 42-second linker 50 comprises subjecting the strand 62 of the ligated first linker 48-miRNA of interest 42-second linker 50 to reverse transcription to produce a double stranded product 64 comprising a first strand 62 of the ligated first linker 48-miRNA of interest 42-second linker 50 and a second strand 66 that is the complement of the first strand 62, where the second strand is hybridized to the first strand. In one embodiment, the second strand 66 is a cDNA of the first strand. In one embodiment, subjecting the strand 62 of the ligated first linker 48-miRNA of interest 42-second linker 50 to reverse transcription to produce a double stranded product 64 is accomplished by standard techniques, as will be understood by those with skill in the art with reference to this disclosure. For example, in one embodiment, subjecting the strand 62 of the ligated first linker 48-miRNA of interest 42-second linker 50 to reverse transcription to produce a double stranded product 64 comprises hybridizing the second linker 50 to a substantially complementary primer 68 having a primer sequence, and comprising between 16 and 25 residues, and further comprising a 3' end 70 capable of being extended by the action of a polynucleotide polymerase, such as a reverse transcriptase, that can use the strand 62 of the ligated first linker 48-miRNA of interest 42-second linker 50 as a template for extension and chain synthesis. In one embodiment, part of the second linker sequence is substantially complementary to a SP6 polynucleotide synthesis promoter motif, and the primer sequence comprises a SP6 promoter sequence that hybridizes to the part of the second linker segment sequence that is substantially complementary to the SP6 polynucleotide synthesis promoter motif. In this embodiment, after the primer 68 has hybridized to the second linker 50, the method comprises contacting the strand 62 of the ligated first linker 48-miRNA of interest 42-second linker 50 with the hybridized primer 68 with a reverse transcriptase, suitable buffers, cofactors and dNTPs (dA, dG, dC, dT or dU) to extend the primer 68, thereby producing the double stranded product 64. As will be understood by those with skill in the art with reference to this disclosure, when the strand 62 of the ligated first linker 48-miRNA of interest 42-second linker 50 subjected to reverse transcription comprises both ribonucleotides and polynucleotides other than ribonucleotides, the polymerase used to effect reverse transcription must be effective on all of the types of polynucleotides present in the strand 62 of the ligated first linker 48-miRNA of interest 42-second linker 50.

In one embodiment, sequencing comprises amplifying the double stranded product 64 to produce amplification products. In a preferred embodiment, amplification is accomplished by standard techniques, as will be understood by those with skill in the art with reference to this disclosure. For example, in one embodiment, amplifying comprises using PCR, according to techniques well known to those with skill in the art.

In one embodiment, the strand 62 of the ligated first linker 48-miRNA of interest 42-second linker 50 is circularized as disclosed above, the first linker sequence, or the second linker sequence, or both the first linker sequence and the second linker sequence comprise an N4 RNA polymerase promoter, and the method further amplifying the circularized ligated strand of the first linker 48-miRNA of interest 42-second linker 50 with N4 RNA polymerase (Epicentre Biotechnologies) to produce RNA runoff sequences. The runoff sequences are linearly amplified representations of the miRNAs in the sample such that the amounts of miRNAs relative to one another in the sample is the same as the amounts of runoff sequences produced relative to one another, though, of course, the concentration of the runoff sequences are increased with respect to the concentrations of their corresponding miRNAs present in the sample.

In one embodiment, sequencing the miRNA of interest 42 of the strand of ligated first linker 48-miRNA of interest 42-second linker 50 comprises cloning the amplification products and culturing the amplification products as isolated colonies to provide a library of miRNAs for further study or for the production of RNAi molecules for each miRNA, according to techniques well known to those with skill in the art, as will be understood by those with skill in the art with reference to this disclosure.

EXAMPLE I

Method for Isolating miRNAs

According to one embodiment of the present invention, the method for isolating microRNAs (miRNAs) was performed as follows. First, eight capture probes were designed, SEQ ID NO:13 through SEQ ID NO:20 as shown in Table III, comprising first adapter segment sequences of SEQ ID NO:1 where the 5'-most residue was biotinylated, second adapter segment sequences of SEQ ID NO:2, and miRNA binding segment sequences that were the exact complement to eight known human miRNAs from a public database. The capture probes were produced by Integrated DNA Technologies according to embodiments of the present invention, and were resuspended in 0.1×TE buffer with 2% Acetonitrile (Sigma Aldrich Corp.; St. Louis, Mo. US) for a final concentration of each capture probe of 100 pmol/µl.

TABLE III

CAPTURE PROBE SEQUENCES

| SEQ ID NO: | Capture Probe Sequence 5'-3' | miRNA Captured by the Capture Probe |
|---|---|---|
| SEQ ID NO: 13 | ATTTAGGTGACACTATAGAAAC TATACAACCTACTACCTCACCC TATAGTGAGTCGTATTA | hsa-let-7a |
| SEQ ID NO: 21 | ATTTAGGTGACACTATAGAACT ATACAACCTACTACCTCACCCT ATAGTGAGTCGTATTA | hsa-let-7e |
| SEQ ID NO: 22 | ATTTAGGTGACACTATAGAGCT ACCTGCACTGTAAGCACTTTTC CCTATAGTGAGTCGTATTA | hsa-miR-106a |
| SEQ ID NO: 23 | ATTTAGGTGACACTATAGACGC GTACCAAAAGTAATAATGCCCT ATAGTGAGTCGTATTA | hsa-miR-126* |
| SEQ ID NO: 24 | ATTTAGGTGACACTATAGATCA CATAGGAATAAAAAGCCATACC CTATAGTGAGTCGTATTA | hsa-miR-135a |
| SEQ ID NO: 25 | ATTTAGGTGACACTATAGAGAT TCACAACACCAGCTCCCTATAG TGAGTCGTATTA | hsa-miR-138 |
| SEQ ID NO: 26 | ATTTAGGTGACACTATAGACGA AGGCAACACGGATAACCTACCC TATAGTGAGTCGTATTA | hsa-miR-154 |
| SEQ ID NO: 27 | ATTTAGGTGACACTATAGAAAT AGGTCAACCGTGTATGATTCCC TATAGTGAGTCGTATTA | hsa-miR-154* |

Next, eight miRNAs having sequences SEQ ID NO:28 through SEQ ID NO:35 that were the exact complements of the miRNA binding segment sequences SEQ ID NO:13, and SEQ ID NO: 21 through SEQ ID NO:27 of the capture probes were obtained from Integrated DNA Technologies as indicated in Table IV. Each of the miRNAs as given in Table IV were prepared from ribonucleotides.

TABLE IV miRNAs ISOLATED BY THE METHOD

| | miRNA Sequence 5'-3' | miRNA Name |
|---|---|---|
| SEQ ID NO: 28 | UGAGGUAGUAGGUUGUAUAGUU | hsa-let-7a |
| SEQ ID NO: 29 | UGAGGUAGGAGGUUGUAUAGU | hsa-let-7e |
| SEQ ID NO: 30 | AAAAGUGCUUACAGUGCAGGUAGC | hsa-mi-106a |
| SEQ ID NO: 31 | CAUUAUUACUUUUGGUACGCG | hsa-mi-126* |
| SEQ ID NO: 32 | UAUGGCUUUUUAUUCCUAUGUGA | hsa-mi-135a |
| SEQ ID NO: 33 | UAGGUUAUCCGUGUUGCCUUCG | hsa-mi-138 |
| SEQ ID NO: 34 | UAGGUUAUCCGUGUUGCCUUCG | hsa-mi-154 |
| SEQ ID NO: 35 | AAUCAUACACGGUUGACCUAUU | hsa-miR-154* |

Then, each miRNA, SEQ ID NO:28 through SEQ ID NO:35, was resuspended in a stabilization buffer containing 1 mM Sodium Citrate pH 6.8 (Ambion, Inc.) and 1 mM aurine tricarboxylic acid (Sigma Aldrich Corp.) to a final concentration of 100 pmol/µl for each miRNA. Next, each of the miRNAs, SEQ ID NO:28 through SEQ ID NO:35, was aliquoted into 10 µl working stocks in 0.5 metal laminate 30 tubes (Nalge Nunc International; Rochester, N.Y. US) to reduce freeze-thaw effects.

Then, the miRNA (hsa-miR-138), SEQ ID NO:33, was hybridized to the capture probe SEQ ID NO:25 by placing the following components into 2.0 metal laminate 30 polypropylene screw cap tubes (Starstedt, Inc.; Newton, N.C. US): 10 pmol of the capture probe SEQ ID NO:25, 1 pmol of miRNA SEQ ID NO:33, 1 metal laminate 30 of 1× Lysis Buffer (5 mM aurine tricarboxylic acid, 10 mM MOPS, 500 mM lithium chloride, and 10 mM EDTA and 1% SDS). Next, the tube was briefly pulsed in a centrifuge to mix the components. Then, the tube was left at room temperature for 10 minutes with occasional inversion of the tube to further mix the components, at which time hybridization of the miRNA SEQ ID NO:33 to the capture probe, SEQ ID NO:25, was essentially total, producing a "capture probe with hybridized miRNA."

Next, the capture probe with hybridized miRNA was coupled to a solid phase As indicated above, the capture probe portion, SEQ ID NO:25, of the capture probe with hybridized miRNA was biotinylated at the 5' end. The capture probe with hybridized miRNA was coupled to a solid phase of streptavidin-coated, paramagnetic beads by adding 20 µl of Streptavidin MagneSphere® paramagnetic particles (Promega Corp.) to the 2.0 metal laminate 30 tube containing the capture probe with hybridized miRNA. Then, the tube was placed on a small tube rotator (Glas-Col, L.L.C.; Terre Haute, Ind. US) set at 20% for 30 minutes at room temperature, resulting in "capture probe with hybridized miRNA bound to the solid phase."

Next, the capture probe with hybridized miRNA bound to the solid phase was separated from the remaining components in the tube by adding a magnet assembly to the cap of the tube, and inverting the tube with the magnet assembly in order to collect the capture probe with hybridized miRNA bound to the solid phase in the cap. The tube with magnet assembly was placed upright to permit fluid to drain from the cap, and then, the magnetic cap assembly was placed on a new 2.0 metal laminate 30 tube containing 200 µl of Wash Buffer A (10 mM Tris-HCl pH 7.5, 500 mM LiCl, 10 mM EDTA pH 8, and 0.1% LiDS). Next, the capture probe with hybridized miRNA bound to the solid phase was resuspended in the Wash Buffer A by removing the magnet from the cap and gently flicking the tube. Once resuspended, the entire volume was transferred to a 0.45 micron Lida filter spin column (Nalge Nunc International) that was placed in a 1.5 metal laminate 30 collection tube. Then, the filter spin column in the collection tube containing the capture probe with hybridized miRNA in Wash Buffer A was centrifuged at 1,000×g for 1 minute, the flow through discarded, and the filter spin column placed back in the collection tube. Next, the capture probe with hybridized miRNA was washed by adding 100 µl of the Wash Buffer B (10 mM Tris-HCl pH 7.5, 500 mM LiCl, and 10 mM EDTA) to the filter spin column in the collection tube, followed by spinning the filter spin column for 1 minute at 1,000×g. The flow through was discarded and the filter spin column containing the capture probe with hybridized miRNA was placed back in the collection tube.

To facilitate downstream analysis, a first linker segment having a first linker segment sequence of (5'-3') taatacgact-cactataggg, SEQ ID NO:36, which comprised a T7 promoter sequence, and a second linker having a second linker segment sequence of (5'-3') tctatagtgtcacctaaat, SEQ ID NO:37, which comprised a SP6 promoter sequence which was phosphorylated at the 5' end, were hybridized, respectively, to the first adapter segment and second adapter segment of the capture probe portion of the capture probe with hybridized miRNA; and the 3' end of the first linker was ligated to the 5' end of the miRNA that was hybridized to the capture probe, and the 5' end of the second linker was ligated to the 3' end of the miRNA that was hybridized to the capture probe, producing a "complex" of a strand of first linker, miRNA and second linker that were ligated together ("strand of ligated first linker-miRNA-second linker"), where the strand is hybridized to the capture probe. Hybridization and ligation of the first linker segment and second linker segment was performed by adding 20 µl of ligation reaction mix 1× rapid ligase buffer (Promega Corp.), 5 pmol of first linker segment, SEQ ID NO:36, (Integrated DNA Technologies), 5 pmol of second linker segment, SEQ ID NO:37, (Integrated DNA Technologies), and 1 unit of T4 polynucleotide ligase (Promega Corp.) and 25% glycerol) to the filter spin column in the collection tub, and allowing the mixture to stand at room temperature for 15 minutes. Then, the reaction was stopped by adding 200 µl of Wash Buffer B and spinning at 1,000×g for 1 minute. The flow through was discarded, and the filter spin column was placed back into the collection tube.

Next, in order to digest and remove excess first linker segments, SEQ ID NO:36, and second linker segments, SEQ ID NO:37, 20 µl of ExoSAP-IT™ (USB Corp.; Cleveland, Ohio US) digest mix containing 17 µl of sterile DI H₂O, 1 µl of ExoSAP-IT™ and 2 µl of 10×PCR Buffer (Applied Biosciences; Foster City, Calif. US) was added to each tube and placed in a 37° C. incubator for 30 minutes. The digested product was washed off and removed by adding 200 µl of Wash Buffer B to each tube, and centrifuging the tube at 1,000×g for 1 minute. The flow through was discarded, and the filter spin column was placed back into the collection tube.

Then, the capture probe, SEQ ID NO:25, was dehybridized from the strand of ligated first linker-miRNA-second linker by adding 20 µl of elution buffer (10 mM Tris-HCl, pH 7.5) that had been pre-heated to 80° C. to the filter spin column, and incubating the filter spin column for 1 minute at room temperature. Next, the filter spin column was spun at 1,000×g for 1 minute. The flow through containing the strand of ligated first linker-miRNA-second linker was removed from the collection tube and placed into a new 1.5 metal laminate 30 screw cap tube (Starstedt, Inc.), and then stored in a −80° C. freezer until further use, completing the method for isolating miRNAs.

EXAMPLE II

Method for Identifying miRNAs

According to one embodiment of the present invention, the method for identifying microRNAs (miRNAs) was performed as follows. First, an miRNA having an miRNA sequence of SEQ ID NO:33 was isolated as part of a strand of the ligated first linker-miRNA-second linker, as disclosed in Example I.

Next, a cDNA copy of the ligated first linker-miRNA-second linker was made by reverse transcription. Reverse transcription was performed by, first, annealing an SP6 primer, (5'-3') CGATTTAGGTGACACTATAG, SEQ ID NO:38 (Integrated DNA Technologies) to the ligated first linker-miRNA-second linker, by adding 5 µl of the ligated first linker-miRNA-second linker to 1 µl of 100 pmol of the SP6 primer, 1 µl of dNTP mix containing 100 mM of each dNTP (Promega Corp.), and 7 µl of sterile DI $H_2O$. These components were put into a 0.7 metal laminate 30 PCR reaction tube (Applied Biosystems) and placed on an MJ Research Thermocycler (Bio-Rad Inc.; Hercules, Calif. US) using calculated control and heated lid at 65° C. for 5 minutes, and then immediately placing the tube on ice for 1 minute. While on ice, Superscript™ III (Invitrogen Corp.) reaction mix (4 µl 5× First Strand Buffer, 1 µl 0.1 M DTT, and 1 µl of 200 units/µl Superscript™ III Reverse Transcriptase) was added to the tube, and then briefly pulsed in a centrifuge to mix the components. Then, cDNA synthesis was performed by incubating the tube on a thermocycler at 50° C. for 30 minutes, and heating to 70° C. for 15 minutes to terminate the reaction.

Next, the cDNA that was synthesized was amplified by PCR. PCR was performed using 5 µl of the cDNA and a PCR buffer containing 10 pmoles each of a forward primer (T7), (5'-3') TAATACGACTCACTATAGGG, SEQ ID NO:39, and a reverse primer (SP6), (5'-3') CGATTTAGGTGACACTATAG, SEQ ID NO:38, 10% 10×PCR buffer (PE Biosystems; Foster City, Calif. US), 2 mM $MgCl_2$ (PE Biosystems), 2% Dimethyl Sulfoxide (Sigma Aldrich Corp.), 5 mM DTT (Bio-Rad Inc.; Hercules, Calif. US), 200 uM of each dNTP (Promega Corp.), and 0.625 units of TaqGold (PE Biosystems) in a total volume of 20 µl. These reaction components were assembled in a 96-well multiplate (Bio-Rad Inc.), and briefly pulsed in a centrifuge to mix components and placed on a thermocycler (Bio-Rad Inc.). Cycling was performed using calculated control and a heated lid with cycles comprising 95° C. for 12 minutes, followed by 30 cycles comprising 95° C. for 30 seconds, 53.5° C. for 20 seconds, 72° C. for 30 seconds, with a final extension at 72° C. for 6 minutes.

Then, electrophoresis was performed to determine the quality of the amplicons using 2 µl of PCR product run on precast Nuseive/GTG 3:1 agarose gels containing ethidium bromide (BMA Corp.; Rockland, Me. US). The band observed on the gel was consistent with size and intensity for the expected amplification polynucleotide product.

Next, in order to digest excess primers, 5 µl of ExoSAP-ITT (USB Corp.) digest mix (3.25 µl of sterile DI $H_2O$, 1.5 µl of ExoSAP-IT™ and 0.25 µl of 100× Acetylated Bovine Serum Albumin (Promega Corp.) per 20 µl reaction) was then added to each well. The plates were then briefly pulsed in a centrifuge to mix components, sealed, and placed on the thermocycler. Incubation was performed using block control and a heated lid with cycles comprising 37° C. for one hour, 65° C. for 10 minutes, and 80° C. for 10 minutes.

Then, the amplified cDNA was cloned into a vector and allowed to grow. Cloning of the amplified cDNA was performed using Zero Blunt® TOPO® PCR Cloning Kit (Invitrogen Corp.). 0.5 µl of PCR product was added to 0.8 µl pCR®-Blunt II-TOPO® vector in a 1.5 metal laminate 30 tube (Starstedt, Inc.), briefly pulsed in a centrifuge to mix components, and incubated at room temperature for 5 minutes. Next, 50 µl of competent DH5alpha-T1 cells was added to the tube and placed on a thermocycler using calculated control and heated lid, and a program comprising 4° C. for 30 minutes, 42° C. for 30 seconds, 15° C. for 4 minutes and 4° C. for 10 minutes. After the transformation was complete, 750 µl of CircleGrow® (Qbiogene, Carlsbad, Calif. US) media with 100 ug/metal laminate 30 Ampicillin (Sigma Aldrich Corp.) was added to the transformation reaction. Next, the tubes were placed in a shaker at 200× rpm at 37° C. for 90 minutes.

Then, the cloned cDNA was amplified by PCR by, first, lysing 1 µl of the transformed DH5alpha culture with 4 µl of Sterile DI H20 in 0.2 metal laminate 30 PCR strip tubes (Fisher Scientific International, Inc.; Hampton, N.H. US) using the thermocycler programmed to 80° C. for 5 minutes, 95° C. for 5 minutes and 4° C. for 5 minutes. Amplification was conducted using 5 µl of the lysed clone culture and a PCR buffer containing 10 pmoles each of forward primer M13-20, (5'-3') GTAAAACGACGGCCAGTG, SEQ ID NO:40, and the reverse primer M13 REV. (5'-3') GGAAACAGCTATGACCATGA, SEQ ID NO:41, 10% 10×PCR buffer (PE Biosystems), 2 mM $MgCl_2$ (PE Biosystems), 2% Dimethyl Sulfoxide (Sigma Aldrich Corp.), 5 mM DTT (Bio-Rad Inc.), 200 uM of each dNTP (Promega Corp.), and 0.625 units of TaqGold (PE Biosystems) in a total volume of 20 µl. The reaction components were assembled in 96-well multiplate (Bio-Rad Inc.) and briefly pulsed in a centrifuge to mix the components. Cycling was performed using calculated control and a heated lid with cycles comprising 95° C. for 12 minutes, followed by 35 cycles comprising 95° C. for 30 seconds, 59.2° C. for 20 seconds, 72° C. for 30 seconds, with a final extension at 72° C. for 6 minutes.

Then, electrophoresis was performed to determine the quality of the amplicons using 2 µl of PCR product run on precast Nuseive/GTG 3:1 agarose gels containing ethidium bromide (BMA Corp.). The band observed on the gel was consistent with size and intensity for the expected amplification polynucleotide product.

Next, in order to digest excess primers, 5 l of ExoSAP-IT™ (USB Corp.) digest mix (3.25 l of sterile DI H2O, 1.5 l of ExoSAP-IT™ and 0.25 l of 100× Acetylated Bovine Serum Albumin (Promega Corp.) per 20 l reaction) was then added to each well. The plates were then briefly pulsed in a centrifuge to mix components, sealed, and placed on the thermocycler. Incubation was performed using block control and a heated lid with cycles comprising 37° C. for one hour, 65° C. for 10 minutes, and 80° C. for 10 minutes.

Then, the amplified cDNA was sequenced using 3 µl of each amplicon, 1.4 pmoles each of primer SEQ ID NO:40 and SEQ ID NO:41, and 2 µl of BigDye Terminator Ready Reactions mix version 3.0® (Applied Biosystems) per 10 µl reaction. The reactions were set up using each PCR primer in both the forward and reverse orientation. The reaction components were assembled in MJ Research 96-well Multiplate and briefly pulsed in a centrifuge to mix. Cycling was performed using calculated control and a heated lid with cycles comprising 95° C. for 5 minutes, followed by 35 cycles comprising 95° C. for 30 seconds, 55° C. for 20 seconds, and 60° C. for 4 minutes.

The finished sequence reaction plate was pulsed in a centrifuge and 1 unit of shrimp alkaline phosphatase (USB Corp.) was added to each well. The plate was pulsed again and incubated at 37° C. for 30 minutes. Next, 10 ml of 10% 1-Butanol was added to each well. The plate was then pulsed to mix and samples were transferred to a Sephadex® (Sigma Chemical Corp.) matrix for dye removal. The Sephadex® matrix was constructed by filling the wells of a 45 µl Multiscreen Column Loader® (Millipore Corp.; Billerica, Mass. US) inverting it into a Multiscreen Plate® (Millipore) and filling each well with 300 µl DI $H_2O$ followed by placement at 4° C. for a minimum of 24 hours prior to use to allow the gel to completely swell. Before use, excess water was spun out of the plate by centrifugation at 900×g for 5 minutes using the S2096 rotor on an Allegra™ 21 Centrifuge (Beckman Coulter Inc.; Fullerton, Calif. US) After samples were transferred to the Sephadex® matrix, a MicroAmp Optical 96-well Reaction Plate (Applied Biosystems) was placed under the Sephadex® plate and the cleaned samples were collected by spinning the two plates again at 900×g for 5 minutes. The plate containing the collected samples, was spun in a SpeedVac® (Telechem International, Inc.) until completely dried. 10 ml of DI Formamide was added to each well and the plate was cycled on a thermalcycler at 95° C. for 5 minutes, 80° C. for 5 minutes, and 4° C. for 5 minutes to resuspend and denature the cDNA. Then, the plate was placed on an ABI Prism® 3700 DNA Analyzer (Applied Biosystems) using Dye Set "H," mobility file "DT3700Pop5(BDv3)v1.mob," cuvette temperature 48° C., injection time 2000 seconds, and injection temperature 45° C. Sequences were then analyzed using Sequencher 4.5 (Gene Codes Corp., Ann Arbor, Mich. US) for basecalling and contig alignment.

Figure 7:
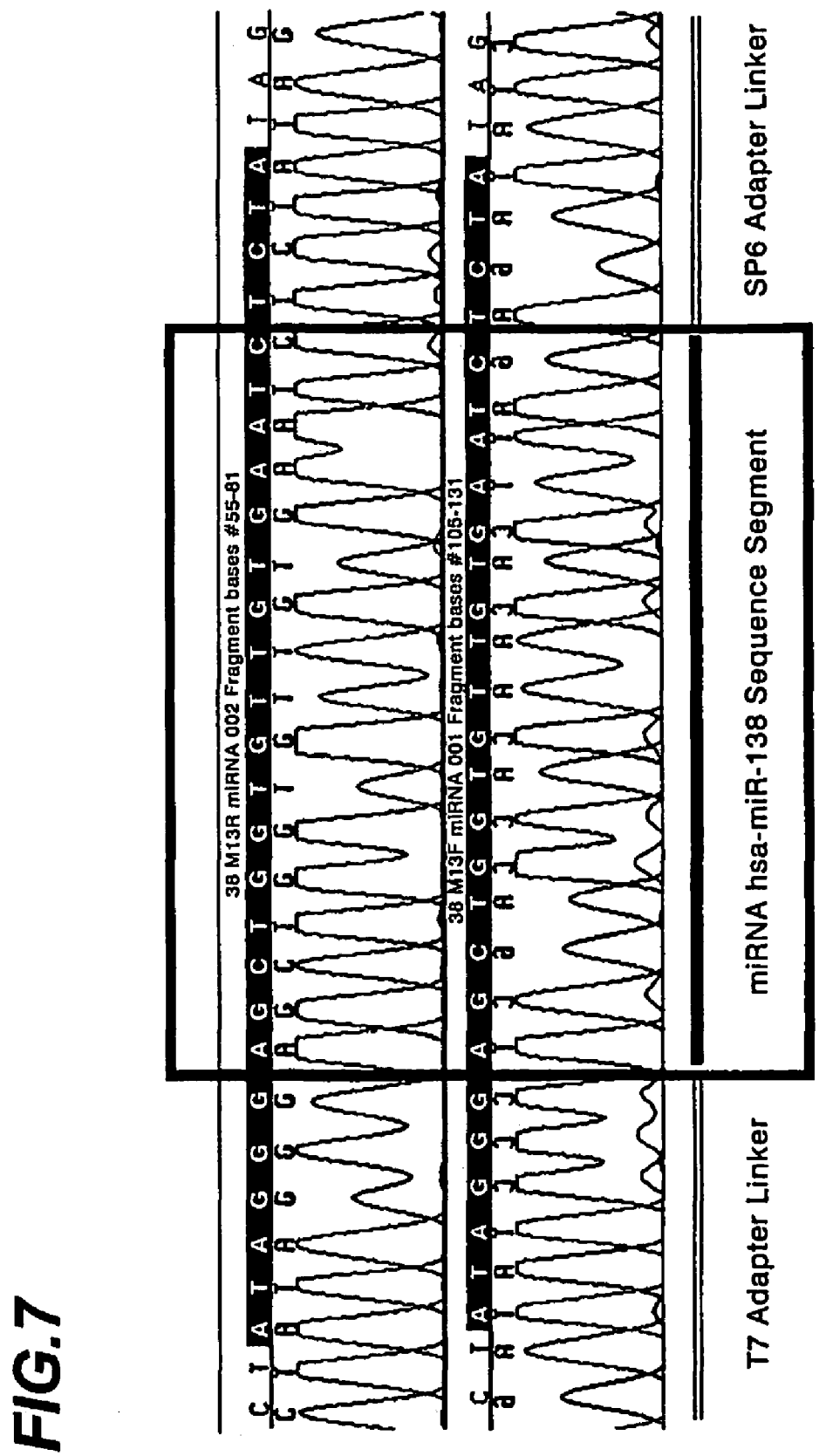
FIG. 7 shows a sequence trace of the miRNA isolated according to the present invention compared to a reference sequence of human miRNA.

Referring now to FIG. 7, there is shown a sequence trace of the cDNA, indicating that the miRNA (hsa-miR-138), SEQ ID NO:33 was successfully isolated and identified by the methods of the present invention.

Using techniques corresponding to the above examples, all of the eight capture probes of the capture probes SEQ ID NO:13, and SEQ ID NO:21 through SEQ ID NO:27 were evaluated in a variety of different combinations with one another with respect to their ability to isolate their corresponding synthesized miRNAs, SEQ ID NO:28 through SEQ ID NO:35, and the capture probes were found to be both selective and specific for the isolation of their corresponding synthetic miRNAs according to the present invention.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

---

What is claimed is:

1. A method for isolating a microRNA of interest (42) from a sample comprising the microRNA of interest (42) according to FIG. 1 through FIG. 6; the method comprising:
   a) providing a sample comprising the microRNA of interest (42);
   b) providing a capture probe (10) comprising:
      i) a first adapter segment (12) having a first adapter segment sequence, the first adapter segment comprising a 3' end (18) and a 5' end (20);
      ii) a second adapter segment (14) having a second adapter segment sequence, the second adapter segment comprising a 3' end (30) and a 5' end (32); and
      iii) a microRNA binding segment (16) having a microRNA binding segment sequence;
      where the microRNA binding segment (16) is substantially complementary to, and capable of hybridizing to, one or more than one microRNA of interest (42) by Watson-Crick base pairing;
      where the 5' end of the first adapter segment (20) is connected to the 3' end of the microRNA binding segment (22); and
      where the 3' end of the second adapter segment (30) is connected to the 5' end of the microRNA binding segment (32);
   c) providing a first linker (48), wherein the first linker has a first linker sequence, comprises a 3' end (52) and a 5' end (54), and is substantially complementary to, and capable of hybridizing to, the first adapter segment (12) of the capture probe (10);
   d) providing a second linker (50), wherein the second linker has a second linker sequence, comprises a 3' end (56) and a 5' end (58), and is substantially complementary to, and capable of hybridizing to, the second adapter segment (14) of the capture probe (10);
   e) combining the sample, the capture probe (10), the first linker (48) and the second linker (50) in a solution;
   f) allowing the first linker (48) to hybridize with the first adapter segment (12), the microRNA of interest (42) to hybridize with the microRNA binding segment (16), and the second linker (50) to hybridize with the second adapter segment (14);
   g) ligating the 3' end of the first linker (52) to the 5' end of the microRNA of interest (46), and ligating the 3' end of the microRNA of interest (44) to the 5' end of the second linker (58), thereby producing a complex defined as a strand of first linker, microRNA of interest and second linker that have been ligated together (ligated first linker (48)-microRNA of interest (42)-second linker (50)) (62) and that is hybridized to the capture probe (10);
   h) dehybridizing the capture probe (10) from the strand of the ligated first linker-microRNA of interest-second linker (62); and
   i) purifying the ligated first linker-microRNA of interest-second linker (62), thereby purifying the microRNA of interest (42).

2. The method of claim 1, where the sample further comprises one or more than one substance that is chemically related to the microRNA of interest selected from the group consisting of an RNA other than a microRNA and a DNA.

3. The method of claim 1, where the sample is from a eukaryote.

4. The method of claim 1, where the sample is from a primate.

5. The method of claim 1, where the sample is from a human.

6. The method of claim 1, where the sample comprises a tissue or fluid selected from the group consisting of blood, brain, heart, intestine, liver, lung, pancreas, muscle, a leaf, a flower, a plant root and a plant stem.

7. The method of claim 1, where the microRNA of interest consists of 18 or 19 or 20 or 21 or 22 or 23 or 24 RNA residues.

8. The method of claim 1, where the microRNA of interest is listed in a public database.

9. The method of claim 1, where the sample provided comprises a plurality of microRNAs of interest; and
   where each of the plurality of microRNAs of interest has microRNA of interest sequences that are identical to one another.

10. The method of claim 1, where the sample provided comprises a plurality of microRNAs of interest comprising a first microRNA of interest having a first microRNA of interest sequence, and a second microRNA of interest having a second microRNA of interest sequence; and
   where the first microRNA of interest sequence is different from the second microRNA of interest sequence.

11. The method of claim 1, where the sample provided comprises a plurality of microRNAs of interest comprising a first microRNA of interest having a first microRNA of interest sequence, a second microRNA of interest having a second microRNA of interest sequence, and a third microRNA of interest having a third microRNA of interest sequence;
   where the first microRNA of interest sequence is different from the second microRNA of interest sequence;
   where the first microRNA of interest sequence is different from the third microRNA of interest sequence; and
   where second microRNA of interest sequence is different from the third microRNA of interest sequence.

12. The method of claim 1, further comprising isolating the total RNA from the sample after providing the sample.

13. The method of claim 1, where the capture probe provided is a set of capture probes;
   where each of the capture probes comprises identical first adapter segment sequences;
   where each of the capture probes of the set of capture probes comprises identical microRNA binding segment sequences; and
   where each of the capture probes of the set of capture probes comprises identical second adapter segment sequences.

14. The method of claim 1, where the capture probe provided is a set of capture probes;
   where the set comprises at least one capture probe comprising a microRNA binding segment that is substantially complementary to, and capable of hybridizing to, each microRNA listed in a single public database.

15. The method of claim 1, where the capture probe provided is a set of capture probes;
   where the first capture probe and the second capture probe have identical first adapter segment sequences;
   where the first capture probe and the second capture probe have identical microRNA binding segment sequences; and
   where the first capture probe has a second adapter segment sequence that is different from the second adapter segment sequence of the second capture probe.

16. The method of claim 1, where the capture probe provided is a set of capture probes;
   where the set comprises a first capture probe and a second capture probe;
   where the first capture probe and the second capture probe have identical first adapter segment sequences;

where the first capture probe and the second capture probe have identical second adapter segment sequences; and where the first capture probe has a microRNA binding segment sequence that is different from the microRNA binding segment sequence of the second capture probe.

17. The method of claim 1, where the capture probe provided is a set of capture probes;
where the set comprises a first capture probe and a second capture probe;
where the first capture probe and the second capture probe have identical microRNA binding segment sequences;
where the first capture probe and the second capture probe have identical second adapter segment sequences; and
where the first capture probe has a first adapter segment sequence that is different from the first adapter segment sequence of the second capture probe.

18. The method of claim 1, where the capture probe provided is a set of capture probes;
where the set comprises a first capture probe and a second capture probe;
where the first capture probe and the second capture probe have identical first adapter segment sequences;
where the first capture probe has a microRNA binding segment sequence that is different from the microRNA binding segment sequence of the second capture probe; and
where the first capture probe has a second adapter segment sequence that is different from the second adapter segment sequence of the second capture probe.

19. The method of claim 1, where the capture probe provided is a set of capture probes;
where the set comprises a first capture probe and a second capture probe;
where the first capture probe and the second capture probe have identical microRNA binding segment sequences;
where the first capture probe has a first adapter segment sequence that is different from the first adapter segment sequence of the second capture probe; and
where the first capture probe has a second adapter segment sequence that is different from the second adapter segment sequence of the second capture probe.

20. The method of claim 1, where the capture probe provided is a set of capture probes;
where the set comprises a first capture probe and a second capture probe;
where the first capture probe and the second capture probe have identical second adapter segment sequences;
where the first capture probe has a first adapter segment sequence that is different from the first adapter segment sequence of the second capture probe; and
where the first capture probe has a microRNA binding segment sequence that is different from the microRNA binding segment sequence of the second capture probe.

21. The method of claim 1, where the capture probe (10) provided is a set of capture probes;
where the set comprises a first capture probe (10) and a second capture probe (10);
where the first capture probe (10) has a first adapter segment sequence (12) that is different from the first adapter segment sequence (12) of the second capture probe;
where the first capture probe has a microRNA binding segment sequence (16) that binds to a microRNA of interest (42) that is different from the microRNA binding segment sequence (16) and the microRNA of interest (42) of the second capture probe; and
where the first capture probe (10) has a second adapter segment sequence (14) that is different from the second adapter segment sequence (14) of the second capture probe (10).

22. The method of claim 1, where the capture probe provided is a set of capture probes;
where the set comprises a first capture probe having a first capture probe sequence, a second capture probe having a second capture probe sequence, and a third capture probe having a third capture probe sequence;
where the first capture probe sequence is different from the second capture probe sequence;
where the first capture probe sequence is different from the third capture probe sequence; and
where second capture probe sequence is different from the third capture probe sequence.

23. The method of claim 1, where the first linker segment and the second linker segment comprise a substance selected from the group consisting of one or more than one type of polynucleotide, one or more than one type of polynucleotide analog, and a combination of one or more than one type of polynucleotide and polynucleotide analog.

24. The method of claim 1, where the first linker, or the second linker, or both the first linker and the second linker are resistant to nuclease degradation.

25. The method of claim 24, where the first linker, or the second linker, or both the first linker and the second linker comprise nuclease resistant nucleotides.

26. The method of claim 24, where the first linker, or the second linker, or both the first linker and the second linker comprise nucleotides with a phosphothioate backbone that render the first linker, or the second linker, or both the first linker and the second linker resistant to nuclease degradation.

27. The method of claim 24, where the first linker, or the second linker, or both the first linker and the second linker comprise nuclease resistant nucleotides and comprise nucleotides with a phosphothioate backbone that render the first linker, or the second linker, or both the first linker and the second linker resistant to nuclease degradation.

28. The method of claim 1, where the first linker and the second linker, each comprises between 6 and 50 residues.

29. The method of claim 1, where the first linker comprises at least 10 residues, and at least 10 residues at the 3' end of the first linker are exactly the complement of the corresponding residues at or near the 5' end of the first adapter segment.

30. The method of claim 1 where the second linker comprises at least 10 residues, and at least 10 residues at the 5' end of the second linker are exactly the complement of the corresponding residues at or near the 3' end of the second adapter segment.

31. The method of claim 1, where the 5' end of the first linker, or the 3' end of the second linker, or both the 5' end of the first linker and the 3' end of the second linker comprise a label.

32. The method of claim 1, where the 5' end of first linker comprises one or more than one residue that extends beyond the 3' end of the first adapter segment after the first linker hybridizes to the first adapter segment.

33. The method of claim 32, where the one or more than one residue of the 5' end of first linker that extends beyond the 3' end of the first adapter segment functions as a primer binding site.

34. The method of claim 1, where the 3' end of second linker comprises one or more than one residue that extends beyond the 5' end of the second adapter segment after the second linker hybridizes to the second adapter segment.

35. The method of claim 34, where the one or more than one residue of the 3' end of second linker that extends beyond the 5' end of the second adapter segment functions as a primer binding site.

36. The method of claim 1, where the sample, the capture probe, the first linker and the second linker are combined simultaneously.

37. The method of claim 1, further comprising adding one or more than one RNAse inhibitor to the combination of the sample, the capture probe, the first linker and the second linker.

38. The method of claim 1, where the first adapter segment comprises a solid phase binding group, or the second adapter segment comprises a solid phase binding group, or both the first adapter segment comprises a solid phase binding group and the second adapter segment comprises a solid phase binding group; and
where the method further comprises binding the capture probe to a solid phase before or after combining the sample, the capture probe, the first linker and the second linker.

39. The method of claim 38, where the solid phase is a plurality of paramagnetic particles.

40. The method of claim 38, where the capture probe is bound to a solid phase through the first adapter segment or through the second adapter segment or through both the first adapter segment and the second adapter segment; and
where the method further comprises purifying the capture probes with hybridized first linker, microRNA of interest and second linker-bound to the solid phase by removing non-hybridized first linkers, second linkers and any other substances that are not bound to the solid phase.

41. The method of claim 38, where the solid phase is contained in a vessel comprising a surface and a cap, and where purifying comprises applying a magnetic field to attract the solid phase to the surface of the vessel or the cap of the vessel.

42. The method of claim 1, where the first linker hybridizes to the first adapter segment at a position where the last residue on the 3' end of the first linker hybridizes to a residue on the first adapter segment that is between 1 residue and 5 residues from the 3' end of the microRNA binding segment.

43. The method of claim 1, where the first linker hybridizes to the first adapter segment at a position where the last residue on the 3' end of the first linker hybridizes to a residue on the first adapter segment that is immediately adjacent to the 3' end of the microRNA binding segment.

44. The method of claim 1, where the second linker hybridizes to the second adapter segment at a position where the last residue on the 5' end of the second linker hybridizes to a residue on the second adapter segment that is between 1 residue and 5 residues from the 5' end of the microRNA binding segment.

45. The method of claim 1, where the second linker hybridizes to the second adapter segment at a position where the last residue on the 5' end of the second linker hybridizes to a residue on the second adapter segment that is immediately adjacent to the 5' end of the microRNA binding segment.

46. The method of claim 1, where the method further comprises purifying the complex.

47. The method of claim 1, where the complex is bound to a solid phase through the first adapter segment or through the second adapter segment or through both the first adapter segment and the second adapter segment; and
where the method further comprises purifying the complex by removing non-hybridized first linkers, second linkers and any other substances that are not bound to the solid phase.

48. The method of claim 1, where the first linker, or the second linker, or both the first linker and the second linker comprise nuclease resistant nucleotides, or comprise nucleotides with a phosphothioate backbone that render the first linker, or the second linker, or both the first linker and the second linker resistant to nuclease degradation; and
where purifying the ligated first linker-microRNA of interest-second linker comprises applying DNAase to a solution containing the ligated first linker-microRNA of interest-second linker to destroy any DNA present in the solution.

49. The method of claim 1, where purifying the ligated first linker-microRNA of interest-second linker comprises circularizing the ligated first linker-microRNA of interest-second linker.

50. A method for identifying a microRNA of interest, the method comprising:
a) isolating the microRNAs according to claim 1; and
b) sequencing the microRNA of interest portion of the strand of the ligated first linker-microRNA of interest-second linker.

51. The method of claim 50, where sequencing comprises subjecting the strand of the ligated first linker-microRNA of interest-second linker to reverse transcription to produce a double stranded product comprising a first strand of the ligated first linker-microRNA of interest-second linker and a second strand that is the complement of the first strand.

52. The method of claim 50, where sequencing comprises amplifying the double stranded product to produce amplification products.

53. The method of claim 51, where sequencing comprises cloning the amplification products and culturing the amplification products.

* * * * *